(12) United States Patent
Petty

(10) Patent No.: US 10,463,734 B2
(45) Date of Patent: Nov. 5, 2019

(54) NANOPARTICLE THERAPY IN CANCER

(71) Applicant: THE REGENTS OF THE UNIVERSITY OF MICHIGAN, Ann Arbor, MI (US)

(72) Inventor: Howard R. Petty, Livonia, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 700 days.

(21) Appl. No.: 14/695,951

(22) Filed: Apr. 24, 2015

(65) Prior Publication Data

US 2015/0335744 A1 Nov. 26, 2015

Related U.S. Application Data

(60) Provisional application No. 61/984,441, filed on Apr. 25, 2014.

(51) Int. Cl.
| | |
|---|---|
| A61K 41/00 | (2006.01) |
| C01G 1/02 | (2006.01) |
| B01J 37/34 | (2006.01) |
| B01J 23/652 | (2006.01) |
| B01J 35/00 | (2006.01) |
| A61K 9/00 | (2006.01) |
| A61K 9/14 | (2006.01) |
| A61K 33/24 | (2019.01) |
| A61K 33/26 | (2006.01) |
| A61K 33/30 | (2006.01) |
| A61N 5/06 | (2006.01) |

(52) U.S. Cl.
CPC ........ *A61K 41/0057* (2013.01); *A61K 9/0009* (2013.01); *A61K 9/143* (2013.01); *A61K 33/24* (2013.01); *A61K 33/26* (2013.01); *A61K 33/30* (2013.01); *B01J 23/6527* (2013.01); *B01J 35/006* (2013.01); *B01J 37/345* (2013.01); *C01G 1/02* (2013.01); *A61N 5/062* (2013.01); *A61N 2005/0662* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 2006/0105910 A1* | 5/2006 | Zhou | ................... | B01J 23/8906 502/338 |
| 2006/0210798 A1* | 9/2006 | Burda | .................... | A61K 33/00 428/402 |
| 2008/0119352 A1* | 5/2008 | Kitaguchi | .......... | B01D 53/8678 502/74 |
| 2009/0191128 A1* | 7/2009 | Ronda | ................ | A61K 41/0057 424/9.4 |
| 2010/0036156 A1* | 2/2010 | Stellacci | ................ | B01J 31/226 562/493 |
| 2010/0262115 A1 | 10/2010 | Madiyalakan et al. | | |

FOREIGN PATENT DOCUMENTS

| | | |
|---|---|---|
| WO | WO-1999/046351 A1 | 9/1999 |
| WO | WO-2011/041107 A1 | 4/2011 |

OTHER PUBLICATIONS

Abe et al., Pristine simple oxides as visible light driven photocatalysts: highly efficient decomposition of organic compounds over platinum-loaded tungsten oxide, *J. Am. Chem. Soc.* 130(25): 7780-1 (2008).
Rye et al., Supporting Information—Pristine simple oxides as visible light driven photocatalysts: Highly efficient decomposition of organic compounds over platinum-loaded tungsten oxide. *J. Am. Chem. Soc.* 130(25): 7780-1 (2008) <http://pubs.acs.org/doi/suppl/10.1021/ja800835q/suppl_file/ja800835q-file002.pdf> retrieved Jun. 30, 2015.
Ackermann et al., Antitumor activity of murine neutrophils demonstrated by cytometric analysis, *Cancer Res.* 49(3): 528-32 (1989).
Araki et al., Na+/H+ exchange modulates rat neutrophil mediated tumor cytotoxicity, *Cancer Res.* 51(12): 3212-6 (1991).
Bao et al., Increased expression of P-glycoprotein is associated with doxorubicin chemoresistance in the metastatic 4T1 breast cancer model, *Am. J. Pathol.* 178(2): 838-52 (2011).
Bhattacharyya et al., Inorganic nanoparticles in cancer therapy. *Pharmaceut Res.* 28(2): 237-59 (2010).
Boya et al., Lysosomal membrane permeabilization in cell death, *Oncogene.* 27(50): 6434-51 (2008).
Chen et al., Collateral damage in cancer chemotherapy: oxidative stress in nontargeted tissues, *Mol. Interv.* 7(3): 147-56 (2007).
Clark et al., Neutrophil-mediated tumor cell cytotoxicity: role of the peroxidase system, *J. Exp. Med.* 141: 1442-7 (1975).
Cross et al., Spontaneous activation of NADPH oxidase in a cell-free system: unexpected multiple effects of magnesium ion concentrations, *Biochem. J.* 338(Pt 1): 229-33 (1999).
D'Autréaux et al., ROS as signalling molecules: mechanisms that generate specificity in ROS homeostasis, *Nat. Rev. Mol. Cell Biol.* 8(10): 813-24 (2007).
Doroshow et al., Role of hydrogen peroxide and hydroxyl radical formation in the killing of Ehrlich tumor cells by anticancer quinones, *Proc. Natl. Acad. Sci. USA* 83(12): 4514-8 (1986).
Dulub et al., Imaging cluster surfaces with atomic resolution: The strong metal-support interaction state of Pt supported on Ti02(110). *Physical Rev. Lett.* 84(16): 3464-9 (2000).
Gerweck et al., Cellular pH gradient in tumor versus normal tissue: potential exploitation for the treatment of cancer, *Cancer Res.* 56(6): 1194-8 (1996).

(Continued)

*Primary Examiner* — Robert A Wax
*Assistant Examiner* — Randeep Singh
(74) *Attorney, Agent, or Firm* — Marshall, Gerstein & Borun LLP

(57) ABSTRACT

Nanoparticles comprising a metal oxide and a platinum cluster having a height to base ratio greater than 1 and compositions containing the same are disclosed. Methods of using the nanoparticles in producing hydroxyl radicals and in photodynamic therapy, for example, in the treatment of hyperproliferative disease such cancer, are also disclosed.

17 Claims, 15 Drawing Sheets

(56) References Cited

OTHER PUBLICATIONS

Gross et al., KMWin—a convenient tool for graphical presentation of results from Kaplan-Meier survival time analysis, *PLoS One.* 7(6): e38960 (2012).

Hasegawa et al., Differential genotoxicity of chemical properties and particle size of rare metal and metal oxide nanoparticles, *J. Appl. Toxicol.* 32(1): 72-80 (2012).

Ishibashi et al., Detection of active oxidative species in TiO2 photocatalysis using the fluorescence technique, *Electrochem. Commun.* 2(3): 207-10 (2000).

Niederkorn et al., Enucleation in consort with immunologic impairment promotes metastasis of intraocular melanomas in mice, *Invest. Ophthalmol. Vis. Sci.* 25: 1080-6 (1984).

Kim et al., Platinized WO3 as an environmental photocatalyst that generates OH radicals under visible light, *Environ. Sci. Techol.* 44(17): 6849-54 (2010).

Lanone et al., Comparative toxicity of 24 manufactured nanoparticles in human alveolar epithelial and macrophage cell lines, *Part. Fibre Toxicol.* 6: 14 (2009).

McKenna et al., Accumulation of immunosuppressive CD11b+ myeloid cells correlates with the failure to prevent tumor growth in the anterior chamber of the eye, *J. Immunol.* 177(3): 1599-608 (2006).

Mediavilla-Varela et al., Docetaxel-induced prostate cancer cell death involves concomitant activation of caspase and lysosomal pathways and is attenuated by LEDGF/p75, *Mol. Cancer.* 8: 68 (2009).

Pompella et al., Imaging of oxidative stress at subcellular level by confocal laser scanning microscopy after fluorescent derivatization of cellular carbonyls, *Am. J. Pathol.* 142: 1353-7 (1993).

Qin et al., Dihydrorhodamine 123 is superior to 2,7-dichlorodihydrofluorescein diacetate and dihydrorhodamine 6G in detecting intracellular hydrogen peroxide in tumor cells, *Cell Biol. Int.* 32(2): 224-8 (2008).

Qourzal et al., Synthesis of TiO2 via hydrolysis of titanium tetraisopropoxide and its photocatalytic activity on a suspended mixture with activated carbon in the degradation of 2-naphthol, *J. Photochem. Photobiol. A: Chem.* 163(3): 317-21 (2004).

Riley, Free radicals in biology: oxidative stress and the effects of ionizing radiation, *Int. J. Radiat. Biol.* 65(1): 27-33 (1994).

Schulze-Osthoff et al., Cytotoxic activity of tumor necrosis factor is mediated by early damage of mitochondrial functions. Evidence for the involvement of mitochondrial radical generation, *J. Biol. Chem.* 267(8): 5317-23 (1992).

Tao et al., Imagable 4T1 model for the study of late stage breast cancer, *BMC Cancer.* 8: 228 (2008).

Vainrub et al., Resolution of 90 nm (lambda/5) in an optical transmission microscope with an annular condenser, *Optics Lett.* 31(19): 2855-7 (2006).

Yamanaka et al., A novel fluorescent probe with high sensitivity and selective detection of lipid hydroperoxides in cells, *RCS Adv.* 2: 7894-900 (2012).

Yamauchi et al., Intracellular hydroxyl radical production induced by recombinant human tumor necrosis factor and its implication in the killing of tumor cells in vitro, *Cancer Res.* 49(7): 1671-5 (1989).

Zamboni et al., Best practices in cancer nanotechnology: perspective from Nci nanotechnology alliance, Clin. Cancer Res. 18(12): 3229-41 (2012).

\* cited by examiner

NANOPARTICLE THERAPY IN CANCER

CROSS-REFERENCE TO RELATED APPLICATION

This application claims the benefit of priority under 35 U.S.C. § 119(e) of U.S. Provisional Patent Application No. 61/984,441 filed Apr. 25, 2014, which is incorporated herein by reference.

STATEMENT OF GOVERNMENT INTEREST

This invention was also made with government support under EY007003 awarded by the National Institutes of Health. The government has certain rights in the invention.

OTHER FUNDING

This invention was made with support from the Mildred E. Swanson Foundation, the Elsa U. Pardee Foundation, The Alliance for Vision Research, Research to Prevent Blindness, and James Thompson and Mary Ann Brandt.

FIELD OF THE INVENTION

The present disclosure relates to nanoparticles comprising a metal oxide and a platinum cluster and their use as therapeutic agents.

BACKGROUND OF THE INVENTION

Many clinical and experimental techniques to treat cancer, such as cytokine therapy, chemotherapy, radiotherapy, cellular immunotherapy, and photodynamic therapy (PDT), promote the formation of reactive oxygen species (ROS). ROS include superoxide anions, hydrogen peroxide, and hydroxyl radicals. ROS participate in the formation of other reactive species. For example, superoxide reacts with nitric oxide to form peroxynitrite, and hydroxyl radicals remove hydrogen atoms from organic compounds to yield reactive carbon-centered radicals. ROS cause oxidative stress leading to cellular damage and cell death. Cytokines, such as tumor necrosis factor, cause apoptotic tumor cell death via intracellular hydroxyl radical production (Schulze-Osthoff et al., *J. Biol. Chem.* 267:5317-23 (1992) and Yamauchi et al., *Cancer Res.* 49:1671-5 (1989)). Many chemotherapeutic drugs induce the production of hydroxyl radicals (Doroshow, J. H., *Proc. Natl. Acad. Sci. USA* 83:4514-8 (1986).), with 56 of 132 FDA-approved anti-cancer drugs promoting oxidative stress (Chen et al., *Mol. Interv.* 7:147-56 (2007)). Radiotherapy causes the formation of hydroxyl radicals by water ionization (Riley, P. A., *Int. J. Radiat. Biol.* 65:27-33 (1994)). For cellular immunotherapy, ROS production by human leukocytes is an important mechanism of tumor cell death in vitro (Clark and Klebanoff, *J. Exp. Med.* 141:1442-7 (1975) and Ackermann et al., *Cancer Res.* 49:52832 (1989)). In the foregoing techniques, ROS effectively kill tumor cells; however, ROS are also deposited within healthy tissues during anticancer therapy, thus causing substantial collateral damage (Chen et al., supra).

In PDT, a photosensitizing agent is administered to a target site in a subject and then irradiated by light of a certain wavelength, which activates the agent and induces the production of ROS to cause toxicity to nearby cells and tissue (see, e.g., U.S. Patent Publication No. 2010/0262115). Nanoparticles can be used as photosensitizing agents and are typically coupled with a chemotherapeutic agent to treat cancer. However, many nanoparticles require ultraviolet (UV) illumination having a wavelength less than 400 nm for activation. Consequently, their use in patient care is precluded by the fact that UV light promotes cancers, such as melanomas, and damage to the eye including pingueculae, cataracts, and other ocular disorders.

There is a need for therapeutic options able to deliver high ROS concentrations to target cells while minimizing damage to healthy tissues and other side effects.

SUMMARY OF THE INVENTION

The present disclosure is directed to nanoparticles comprising a metal oxide and a platinum cluster, wherein the platinum cluster has a height to base ratio greater than 1. In one aspect, the platinum cluster serves as a co-catalyst in the formation of ROS. In various aspects, the platinum cluster comprises platinum oxide. Optionally, the crystal structure of the platinum cluster is not cubic. Also optionally, the surface to volume ratio of the platinum cluster is greater than $1\ nm^{-1}$. In one aspect, the platinum cluster is grafted on the metal oxide.

In one aspect, the nanoparticle comprises a metal oxide selected from the group consisting of tungsten oxide, titanium oxide, zinc oxide, cerium oxide, iron oxide, and combinations thereof. For example, the nanoparticle may comprise a tungsten oxide, such as tungsten trioxide, or a titanium oxide. Optionally, the nanoparticle comprises tungsten trioxide having an orthorhombic crystal structure. In one aspect, the diameter of the nanoparticle is greater than about 20 nm. For example, the diameter of the nanoparticle may be about 50 nm to about 60 nm.

The present disclosure further provides compositions comprising a nanoparticle described herein in combination with a pharmaceutically acceptable carrier. In one aspect, the composition is for use in the treatment of a neoplastic, hyperplastic, or hyperproliferative disease, such as cancer.

The present disclosure also provides a method of making nanoparticles comprising forming a mixture of metal oxide nanoparticles and chloroplatinic acid and then alkalinizing the mixture to a pH above 10, for example to a pH of about 12.

The present disclosure also provides methods of using the nanoparticles. In one aspect, a method of generating hydroxyl radicals comprises irradiating a nanoparticle of the present disclosure with radiation having a wavelength greater than about 400 nm. In another aspect, a method of photodynamic therapy (PDT) comprises administering a therapeutically effective amount of a nanoparticle of the present disclosure to a subject in need thereof and irradiating the nanoparticle with radiation having a wavelength greater than about 400 nm to generate hydroxyl radicals.

The present disclosure also provides a method of treating a neoplastic, hyperplastic, or hyperproliferative disorder in a subject in need thereof. The method comprises administering a therapeutically effective amount of a nanoparticle described herein to the subject and irradiating the nanoparticle with radiation having a wavelength greater than about 400 nm. A method of treating cancer in a subject in need thereof also is provided, the method comprising administering a therapeutically effective amount of a nanoparticle described herein to the subject and irradiating the nanoparticle with radiation having a wavelength greater than about 400 nm. In addition, a method of inhibiting cancer growth or metastasis is provided, which comprises contacting a cancer cell with an effective amount of a nanoparticle described herein and irradiating the nanoparticle with radiation having a wavelength greater than about 400 nm. The cancer is optionally selected from the group consisting of breast cancer, ocular cancer, skin cancer, bladder cancer, esophageal cancer, and lung cancer.

In various aspects, a method of using a nanoparticle of the present disclosure comprises irradiating the nanoparticle with radiation having a wavelength in a range of about 400 nm to about 750 nm or about 750 nm to about 1 mm. The nanoparticles may be administered to a subject in need thereof via any of a number of suitable routes, including intratumorally, intravenously, intraocularly, topically, or subcutaneously.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE DRAWINGS

FIG. 1A depicts a schematic illustration of catalytic reactions. FIG. 1B shows a diagram of an exemplary platinum cluster graft.

FIG. 2A shows HR-TEM images of $WO_3$ nanoparticles. FIG. 2B shows HR-TEM of $WO_3$/Pt nanoparticles. Platinum cluster grafts are indicated with arrows.

FIG. 4A shows the kinetics of 7-Hydroxycoumarin fluorescence appearance for $WO_3$/Pt nanoparticles prepared at alkaline pH (pH of about 12). FIG. 4B shows the kinetics of 7-hydroxycoumarin fluorescence for $WO_3$/Pt nanoparticles prepared at alkaline pH (diamonds), $WO_3$/Pt nanoparticles prepared at a pH of about 2 (circles), and unmodified $WO_3$ nanoparticles (triangles).

FIG. 6A shows conventional bright field microscopy (100× magnification) of untreated tumor cells. FIG. 6B shows a conventional bright field microscopy (100× magnification) of nanoparticle-treated tumor cells. FIG. 6C shows surface plasmon enhanced microscopy (700× magnification) of cells grown in the absence of nanoparticles. FIG. 6D shows surface plasmon enhanced microscopy (700× magnification) of cells incubated with nanoparticles. FIG. 6E shows transmission electron microscopy (TEM) of an untreated tumor cell. FIG. 6F shows TEM of a nanoparticle-treated tumor cell that was not exposed to light. FIG. 6G shows TEM of a nanoparticle-treated tumor cell that was exposed to light therapy for 2 hours. FIG. 6H shows TEM of a nanoparticle-treated tumor cell exposed to light therapy for 5 hours.

FIG. 7A shows dihydrorhodamine 6G-labeled nanoparticle-treated 4T1 cells incubated for 30 minutes in the dark. FIG. 7B shows dihydrorhodamine 6G-labeled nanoparticle-treated 4T1 cells incubated for 30 minutes with visible light (~0.6 lm/cm$^2$). FIG. 7C shows lipid peroxide formation in nanoparticle-treated tumor cells exposed to darkness only. FIG. 7D shows lipid peroxide formation in nanoparticle-treated tumor cells after 20 minutes of light exposure. FIG. 7E shows 4HNE staining in nanoparticle-treated tumor cells exposed to darkness only. FIG. 7F shows 4HNE staining in nanoparticle-treated tumor cells after 20 minutes of light exposure. FIG. 7G shows Lyso-ID Red staining in nanoparticle-treated tumor cells exposed to darkness only. FIG. 7H shows Lyso-ID Red staining in nanoparticle-treated tumor cells after 20 minutes of light exposure. FIG. 7I shows activated caspase 3/7 labeling in nanoparticle-treated tumor cells exposed to darkness only. FIG. 7J shows activated caspase 3/7 labeling in nanoparticle-treated tumor cells after 20 minutes of light exposure.

FIG. 8A shows a micrograph of 4T1 cells treated with light for 3 hours. Dark clusters correspond to regions rich in nanoparticles. FIG. 8B shows the same cells using NAH cytochemistry to observe aldehyde reactive sites. FIG. 8C shows a fluorescence image of 4T1 cells incubated in the dark without nanoparticles. FIG. 8D shows a fluorescence micrograph of cells treated with light for 3 hours, but in the absence of nanoparticles. FIG. 8E shows a fluorescence micrograph of nanoparticle-treated 4T1 cells incubated for 3 hours in the dark.

FIG. 9A shows untreated animals. FIG. 9B shows animals treated with 4T1 cells. FIG. 9C shows animals treated with 4T1 cells and $WO_3$/Pt nanoparticles and ambient light. FIG. 9D shows animals treated with 4T1 cells and $WO_3$/Pt nanoparticles and darkness only. FIG. 9E shows animals treated with 4T1 cells and WO$_3$ nanoparticles and ambient light.

FIG. 10A shows a low power image of a H/E-stained sagittal eye section in a control (untreated) animal. FIG. 10B shows a low power image of a H/E-stained sagittal eye section in an eye treated with nanoparticle-tagged tumor cells and illumination with light. FIG. 10C shows an eye treated with tumor cells alone.

DETAILED DESCRIPTION OF THE INVENTION

Figure 1A:
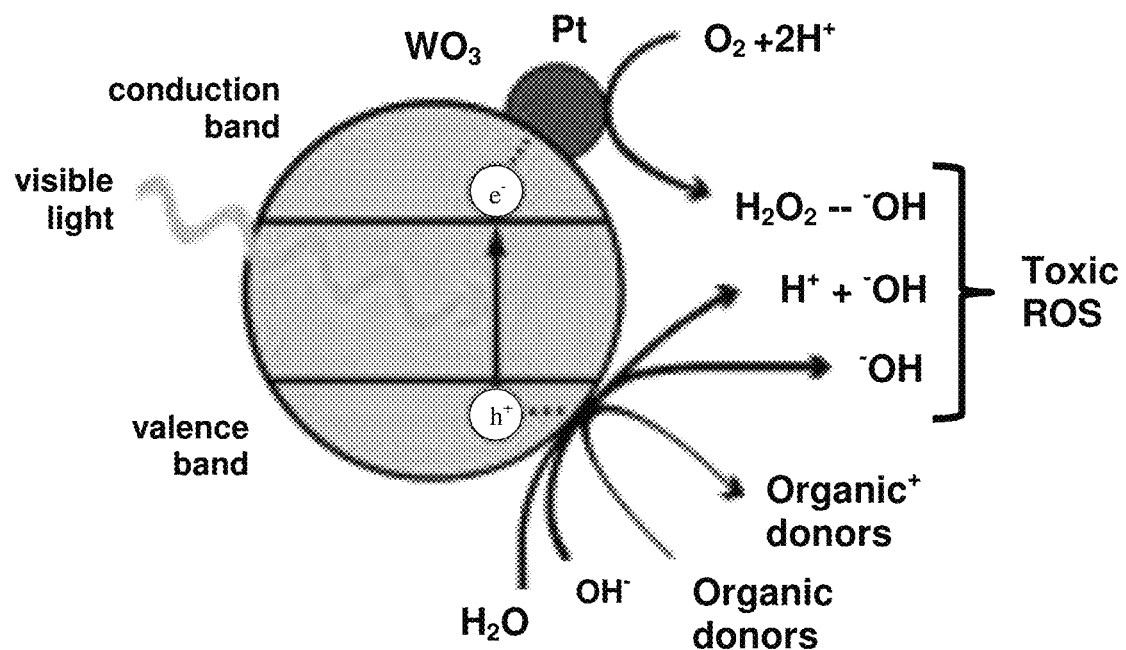
FIGS. 1A-1B depict a schematic illustration of exemplary $WO_3$/Pt nanoparticles.

The present disclosure provides nanoparticles comprising a metal oxide and a platinum cluster, wherein the platinum cluster has a height to base ratio greater than 1. The nanoparticles can be used to generate ROS, such as hydroxyl radicals, by irradiating the nanoparticles with radiation having a wavelength greater than or equal to about 400 nm. The nanoparticles of the present disclosure have numerous advantages compared to conventional therapies, including both physico-chemical advantages and clinical advantages. First, the nanoparticles focus their therapeutic effect directly on a target cell instead of neighboring cells, due to the hydroxyl radicals' high reactivity and small radius of diffusion, thereby minimizing damage to healthy cells. The nanoparticles do not photobleach and thus can be used repeatedly over extended periods of time. Additionally, the nanoparticles exhibit greater chemical activity than current PDT reagents and possess large light absorption cross-sections.

The nanoparticles provide clinical advantages in that they avoid many of the problems that limit the therapeutic efficacy of other anticancer treatments. The nanoparticles are not adversely affected by the tumor microenvironment. The nanoparticles also are not susceptible to multi-drug resistance mechanisms. Because the nanoparticles can be activated by visible light, which is not mutagenic, instead of UV radiation, use of the nanoparticles does not increase the risk of secondary tumors. Unlike other chemotherapeutic agents, the nanoparticles require minimal reagents, allowing high doses to be used in patient care, including for the treatment of patients that are very ill. The nanoparticles are also inexpensive to manufacture and administer.

The following definitions may be useful in aiding the skilled practitioner in understanding the disclosure. Unless otherwise defined herein, scientific and technical terms used in the present disclosure shall have the meanings that are commonly understood by those of ordinary skill in the art.

The term "nanoparticle" refers to a particle having at least one dimension, such as diameter or circumference, which is greater than about 10 nm and less than about 500 nm. A nanoparticle can be any of a number of geometric shapes, e.g., spheres, pyramids, cubes, or rods.

The term "oxide" refers to a chemical compound containing at least one oxygen atom and at least one atom of another element, e.g., a metal. The term encompasses chemical compounds containing one oxygen atom, i.e., monoxides, and more than one oxygen atom, e.g., dioxides, trioxides, and tetraoxides.

The term "platinum cluster" refers to an aggregate of platinum atoms comprising between 1 and 100 platinum nanospikes, optionally between 5 and 25 platinum nanospikes. Each platinum nanospike comprises more than 60 platinum atoms linked by metallic bonding. Nanospikes can have a flat or pointed top.

The "height to base ratio" refers to the axial ratio between the height and base of a platinum cluster. The "height" is defined as the length of the platinum cluster from the point of attachment between the platinum cluster and a metal oxide to the apex of the platinum cluster. The "base" is defined as the width of the platinum cluster at the point of the attachment between the platinum cluster and a metal oxide.

The term "graft" refers to a platinum cluster attached to the surface of a metal oxide molecule, e.g., from the valence band electrons of the platinum and metal oxide forming a shared bond among the valence band electrons. A platinum cluster may be grafted to a metal oxide using deposition methods known in the art.

The terms "therapeutically effective amount" and "effective amount" depend on the condition of a subject and the specific compound(s) administered. The terms refer to an amount effective to achieve a desired biological, e.g., clinical effect. A therapeutically effective amount varies with the nature of the disease being treated, the length of time that activity is desired, and the age and the condition of the subject. In one aspect, a therapeutically effective amount of a nanoparticle or composition of the invention is an amount effective to inhibit growth of hyperproliferative cells, prevent cancer cell metastasis, and/or result in cancer cell death.

The present disclosure provides a nanoparticle comprising a metal oxide and a platinum cluster, wherein the platinum cluster has a height to base ratio greater than 1. In various aspects, the height to base ratio can be between 1 and 2, between 2 and 4, or between 2.5 and 5. For example, the height to base ratio (height:base) can be about 1.1, about 1.2:1, about 1.3:1, about 1.4:1, about 1.5:1, about 1.6:1, about 1.7:1, about 1.8:1, about 1.9:1, about 2:1, about 2.5:1, about 3:1, about 3.5:1, about 4:1, about 4.5:1, or about 5:1. Platinum typically has a face-centered cubic crystal structure. However, above the dimensions of the unit cell, platinum can take on other shapes, such as spherical. Because the height of the platinum cluster on the surface of the metal oxide nanoparticle of the present disclosure is greater than its base, the platinum deposited on the metal oxide has an elongated structure, more similar to a nanospike or obelisk. In one aspect, the minimum surface-to-volume ratio of the platinum cluster is greater than 1 nm$^{-1}$, for example, about 2 nm$^{-1}$. In various aspects, the platinum cluster may comprise a platinum oxide, for example, PtO, PtO$_2$, PtO$_3$, or Pt$_3$O$_4$.

The nanoparticles of the present disclosure do not require ultraviolet radiation and can be activated with visible light, i.e., light having a wavelength greater than about 400 nm, because the energy difference between the valence and conduction bands is small. In one aspect, the nanoparticles are activated by irradiation with light having a wavelength in a range from about 400 nm to about 750 nm, for example, about 400 nm to about 700 nm, about 400 nm to about 500 nm, or about 400 nm to about 450 nm. In another aspect, the nanoparticles can be activated with light having a wavelength in the red or infrared range, i.e., about 750 nm to about 1 mm, and thereby permit tumor destruction at greater depths in opaque tissues. Because the nanoparticles do not require UV light for activation, they avoid the damaging effects of UV radiation and can be selectively activated using ambient light. For example, the nanoparticles can be irradiated by light from an exterior source, e.g., a lamp or light emitting diode (LED), or internally, e.g., using an endoscope.

In one aspect, the platinum cluster is a co-catalyst in the generation of ROS. As shown in FIG. 1A, visible light promotes an electron from the valence band of the metal oxide to its conduction band, thereby creating a valence band hole. Conduction band electrons accumulate at the platinum cluster, which catalyzes the reduction of oxygen to hydrogen peroxide, and then on to hydroxyl radicals. Valence band holes migrate to the surface of the nanoparticle, where they remove electrons from water, hydroxide anions, or organic molecules to create hydroxyl radicals and degrade organic compounds.

In one aspect, a nanoparticle according to the present disclosure comprises a metal oxide selected from the group consisting of tungsten oxide, titanium oxide, zinc oxide, cerium oxide, iron oxide, and combinations thereof. In one aspect, the metal oxide is tungsten oxide, for example, WO, $WO_2$, $WO_3$, $W_2O_3$, $W_4O_5$, or $W_4O_{11}$. In one embodiment, the metal oxide is tungsten trioxide ($WO_3$), optionally having an orthorhombic crystal structure or a tetragonal crystal structure. Platinum-loaded tungsten trioxide nanoparticles ($WO_3$/Pt), a metal oxide semiconductor and metal co-catalyst, display photocatalytic activity (Abe et al., *J. Am. Chem. Soc.* 130:7780-1 (2008)). The valence band holes of $WO_3$ have high oxidation power (+3 $V_{NHE}$) while Pt serves as a co-catalyst in the multi-electron reduction of oxygen to hydroxyl radical. $WO_3$ nanoparticles have little or no toxic effects (Lanone et al., *Part. Fibre Toxicol.* 6:14 (2009) and Hasegawa et al., *J. Appl. Toxicol.* 32:72-80 (2012)), and $WO_3$ has an oral $LD_{50}$ of 1059 mg/kg. In another aspect, the metal oxide is titanium oxide, for example, TiO, $TiO_2$, $Ti_2O_3$, or $TiO_3$.

In one aspect, the nanoparticle has a diameter greater than about 20 nm. For example, the nanoparticle can have a diameter greater than about 25 nm, greater than about 30 nm, greater than about 35 nm, greater than about 40 nm, greater than about 45 nm, greater than about 50 nm, greater than about 55 nm, greater than about 60 nm, greater than about 65 nm, greater than about 70 nm, greater than about 75 nm, greater than about 80 nm, greater than about 85 nm, greater than about 90 nm, greater than about 95 nm, or greater than about 100 nm. In various aspects, the diameter of the nanoparticles is about 50 nm to about 60 nm, about 40 nm to about 80 nm or about 20 nm to about 100 nm. In various aspects, the diameter of the nanoparticles is about 50 nm, about 51 nm, about 52 nm, about 53 nm, about 54 nm, about 55 nm, about 56 nm, about 57 nm, about 58 nm, about 59 nm, or about 60 nm. In one aspect, the nanoparticle is spherical. In another aspect, the nanoparticle is rod-shaped.

In one aspect, the nanoparticle further comprises a surface modification, for example, to attach a ligand to improve delivery of the nanoparticle to a target site. Examples of ligands include, but are not limited to, folate and the anti-epithelial cell adhesion molecule (anti-EpCAM) antibody. In one aspect, the nanoparticle further comprises modification of surface hydroxyl groups, for example, to link the surface hydroxyl groups to the carboxylic acid group of folic acid, e.g., via Fischer esterification, in order to deliver the nanoparticle to a cancer cell expressing a folate receptor, such as a breast cancer cell. Covalent linkage to the nanoparticle via folate's γ-carboxyl moiety does not affect the high affinity binding of folate to the folate receptor and also does not interfere with the hydroxyl radical production of the nanoparticles, allowing for targeted delivery of the nanoparticle to cancer cells in vivo. In another example, the nanoparticle further comprises an anti-EpCAM antibody attached to the nanoparticle surface, in order to deliver the nanoparticle to a cancer cell overexpressing EpCAM molecules. Optionally, the nanoparticle further comprises a ligand attached to the nanoparticle surface via a linker, e.g., a heterobifunctional linker. Optionally, the nanoparticle further comprises a surface modification to provide a biocompatible interface, for example, a poly-L-lysine coating or a polyethylene glycol coating. In one aspect, the interface is adsorbed to the surface of the nanoparticle. In another aspect, the interface is covalently linked to the surface of the nanoparticle. In one aspect, a ligand such as a folate group or anti-EpCAM antibody is linked to the biocompatible interface.

Figure 1B:
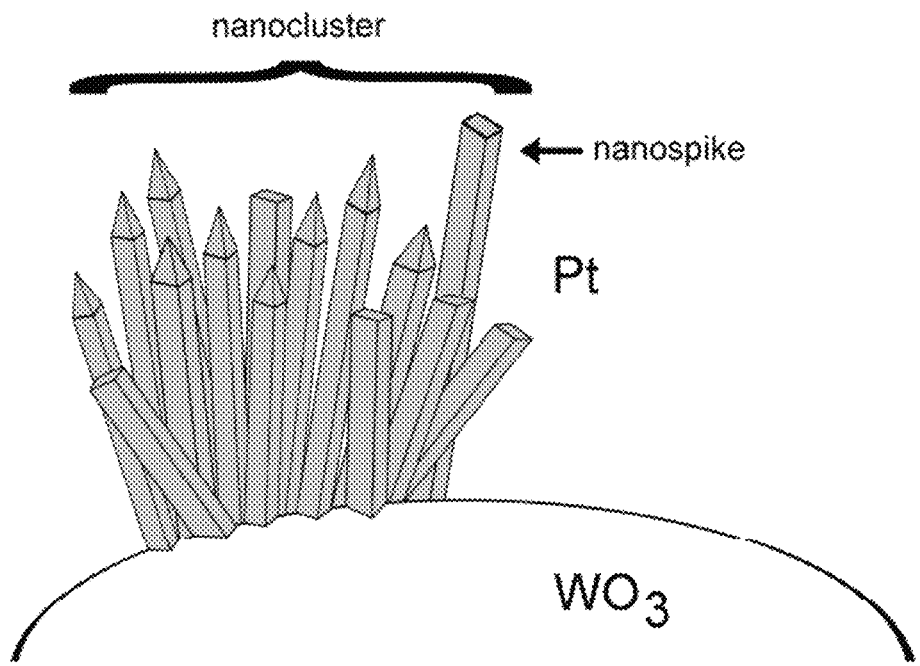

The present disclosure also provides a method of making nanoparticles comprising a metal oxide and a platinum cluster. In one aspect, the platinum cluster is grafted to the metal oxide. FIG. 1B shows a diagram of an exemplary platinum cluster. A platinum cluster is comprised of a plurality of platinum nanospikes, optionally between 1 to 100 nanospikes or between 5 and 25 nanospikes. In one aspect, a nanospike can have a base width of about 1 nm to about 10 nm, for example, about 2 nm, and a height of about 5 to about 20 nm, for example, about 10 nm. The platinum nanospikes and clusters are structurally unique photocathodes.

A method of making nanoparticles according to the present disclosure comprises forming a mixture of a metal oxide nanoparticles and chloroplatinic acid and then alkalinizing the mixture to a pH above 10 to graft platinum clusters on the nanoparticles. For example, the mixture can be alkalinized with NaOH to a pH above 10, e.g., to a pH of about 12. High pH values are known to dissolve some metal oxide, e.g., tungsten trioxide, crystals. In one aspect, a method of making nanoparticles according to the present disclosure comprises exposing metal oxide nanoparticles to a pH above 10 for just long enough to photodeposit the platinum and then exhaustively dialyzing the sample to obtain a neutral pH. In another aspect, a method of making nanoparticles comprises using a reducing agent, e.g., sodium borohydrate, and reducing the nanoparticles in a $H_2$ stream at 480° C. for 15 hours to graft platinum clusters on the nanoparticles.

The present disclosure also provides a composition comprising a nanoparticle described herein in combination with a pharmaceutically acceptable carrier. In one aspect, the composition is for use in the treatment of a neoplastic, hyperplastic, or hyperproliferative disease, such as cancer. Pharmaceutically acceptable carriers include, but are not limited to, water, saline, phosphate buffered saline, and commercial buffers. Preferably, the carrier is sterile. Other excipients, including buffering agents, dispersing agents, and preservatives, are known in the art and may be included in the composition. Further examples of components that may be employed in compositions are presented in Remington's Pharmaceutical Sciences, $16^{th}$ Ed. (1980) and $20^{th}$ Ed. (2000), Mack Publishing Company, Easton, Pa. A composition may be in any suitable dosage form including, but not limited to, tablets, capsules, implants, depots, liquids, patches, lozenges, creams, ointments, lotions, aerosols, and eye drops.

The present disclosure provides methods of using the nanoparticles described herein. In one aspect, a method of generating hydroxyl radicals comprises irradiating a nanoparticle of the present disclosure with radiation having a wavelength greater than about 400 nm. In another aspect, a method of photodynamic therapy (PDT) comprises administering a therapeutically effective amount of a nanoparticle of the present disclosure to a subject in need thereof and irradiating the nanoparticle with radiation having a wavelength greater than about 400 nm to generate hydroxyl radicals.

A method of treating a neoplastic, hyperplastic, or hyperproliferative disorder in a subject in need thereof comprises administering a therapeutically effective amount of a nanoparticle described herein to the subject and irradiating the nanoparticle with radiation having a wavelength greater than about 400 nm. In a further aspect, a method of treating cancer in a subject in need thereof also is provided. The method comprises administering a therapeutically effective amount of a nanoparticle described herein to the subject and irradiating the nanoparticle with radiation having a wavelength greater than about 400 nm. In a further aspect, the cancer is selected from the group consisting of breast cancer, ocular cancer, skin cancer, bladder cancer, esophageal cancer, and lung cancer. One of ordinary skill will appreciate that treating a cancer does not require complete eradication of the cancer. Any beneficial physiologic response is contemplated, such as tumor shrinkage, tumor cell death, reduction or halting of metastasis, reduction in cancer cell markers, alleviation of symptoms and the like. Use of the nanoparticles as an anticancer agent departs from conventional nanoparticle applications in that the nanoparticles of the present disclosure can be the therapeutic agents themselves, not simply a vehicle or magnetic tag for another agent (Zamboni et al., *Clin. Cancer Res.* 18:3229-41 (2012)). In one aspect, a method of inhibiting cancer growth or metastasis comprises contacting a cancer cell with an effective amount of a nanoparticle described herein and irradiating the nanoparticle with radiation having a wavelength greater than about 400 nm. When used to treat cancer, the nanoparticles can also be localized to and activated at tumor sites instead of systemic activation that would expose vital organs. ROS are produced inside tumor cells, resulting in selective toxicity and limited damage to healthy tissue, thus avoiding the side effects of conventional anticancer therapies.

In one aspect of the present methods, a therapeutically effective amount of a nanoparticle or composition described herein, typically formulated in accordance with pharmaceutical practice, is administered to a subject in need thereof. A particular administration regimen for a particular subject will depend, in part, upon the nanoparticle or composition, the amount administered, the route of administration, and the cause and extent of any side effects. The amount administered to a subject (e.g., a mammal, such as a human) in accordance with the invention should be sufficient to effect the desired response over a reasonable time frame. Dosage typically depends upon the route, timing, and frequency of administration. Accordingly, a clinician titers the dosage and modifies the route of administration to obtain the optimal therapeutic effect.

Purely by way of illustration, the methods of the present disclosure comprise administering, e.g., from about 0.1 mg/kg to about 100 mg/kg or more of nanoparticle composition based on the weight of the tumor or subject, depending on the factors mentioned above. In other embodiments, the dosage ranges from about 0.1 mg/kg to about 0.5 mg/kg, about 5 mg/kg to about 75 mg/kg, about 10 mg/kg to about 50 mg/kg, or about 10 mg/kg to about 25 mg/kg. The treatment period will depend on the particular condition and may last one day to several days, weeks, months, or years. A nanoparticle or composition described herein can be administered in an amount of about 10 mg to about 900 mg per dose, about 10 mg to about 30 mg per dose, about 15 mg to about 25 mg per dose, about 20 mg to about 40 mg per dose, about 50 mg to about 500 mg per dose, or about 100 mg to about 250 mg per dose. For example, the nanoparticles can be administered, per dose, in an amount of about 10, about 15, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, or 900 mg, including all doses between about 10 mg and about 900 mg. The above dosages are exemplary of the average case, but there can be individual instances in which higher or lower dosages are merited, and such are within the scope of this invention. In practice, a clinician determines the actual dosing regimen that is most suitable for an individual subject, which can vary with the age, weight, condition and response of the particular subject.

Suitable methods of administering a physiologically acceptable composition, such as a composition comprising a nanoparticle described herein, are well known in the art. Although more than one route can be used to administer a compound, a particular route can provide a more immediate and more effective reaction than another route. Depending on the circumstances, a composition comprising the nanoparticles described herein is introduced into tumor sites, applied or instilled into body cavities, absorbed through the skin or eye or mucous membranes, inhaled, and/or introduced into circulation. The nanoparticles can be injected intravenously, resulting in systemic uptake, and then selectively activated only at tumor sites. Alternatively, the nanoparticles may be administered locally by directly contacting tumor cells with the nanoparticles. For example, in certain circumstances, it will be desirable to deliver the composition through injection or infusion by intravenous, intratumoral, intraperitoneal, intracerebral (intra-parenchymal), intracerebroventricular, intramuscular, intraocular, intraarterial, intraportal, intralesional, intramedullary, intrathecal, intraventricular, transdermal, subcutaneous, intraperitoneal, intranasal, transdermal, enteral, topical, sublingual, urethral, vaginal, or rectal means; by controlled, delayed, sustained or otherwise modified release systems; or by implantation devices. If desired, the composition is administered regionally via intratumoral administration, intraocular administration, intrathecal administration, intracerebral (intra-parenchymal) administration, intracerebroventricular administration, topical administration, subcutaneous administration or intraarterial or intravenous administration targeting the region of interest. Alternatively, the composition is administered locally via implantation of a matrix, membrane, sponge, or another appropriate material onto which the nanoparticles have been absorbed or encapsulated. Where an implantation device is used, the device is, in one aspect, implanted into any suitable tissue or organ, and delivery of the desired compound is, for example, via diffusion, timed-release bolus, or continuous administration.

In one aspect, the nanoparticles can be administered intraocularly to treat eye diseases including retinoblastoma, lymphoma, medulloepithelioma, hemangioma, intraocular melanoma, and ocular metastases. Eye cancers are among the most difficult to treat, and are typically treated with surgery, including removal of the eye. The nanoparticles of the present disclosure can be used to selectively deliver high levels of ROS to shrink the tumor and provide an alternative to surgery. In another aspect, the nanoparticles can be administered topically, transdermally, or subcutaneously to treat skin diseases. For example, the nanoparticles can be used to treat skin cancers including basal and squamous cell cancers and melanoma. Additionally, the nanoparticles may be used to treat skin disorders such as systemic sclerosis, which is fibrosis of the skin. The disease is extremely difficult to manage and often relies on immunosuppressants to stop the growth and activation of myofibroblasts. The nanoparticles are optionally targeted to inhibit myofibroblasts and control the disorder. The nanoparticles can be readily and non-invasively activated with visible light at the target sites on the eye or skin, thereby avoiding the damaging effects of UV radiation. In another aspect, the nanoparticles are used to treat localized infections.

Following administration of the nanoparticles, there may be an incubation period of at least several hours, e.g., 2 to 4 hours or more, to allow for uptake of the nanoparticles into target cells, before the nanoparticles are irradiated. The irradiation dose may be between about 1 $J/cm^2$ and 100 $J/cm^2$, for example, between about 1 $J/cm^2$ and about 60 $J/cm^2$, between about 50 $J/cm^2$ and about 60 $J/cm^2$, or between about 1 $J/cm^2$ and about 5 $J/cm^2$. Depending on the condition to be treated and the dose, nanoparticles may be irradiated with light for between about 10 minutes and about 120 minutes, between about 20 minutes and about 60 minutes, or between about 30 minutes and about 90 minutes. For example, the nanoparticles may be irradiated for about 10 minutes, about 20 minutes, about 30 minutes, about 40 minutes, about 45 minutes, about 50 minutes, about 60 minutes, about 70 minutes, about 80 minutes, about 90 minutes, about 100 minutes, about 110 minutes, or about 120 minutes. Because the nanoparticles are not metabolized or otherwise degraded and do not photobleach, the nanoparticles may also be irradiated with light repeatedly following a single dose. In various aspects, there may be intervals of several hours to days between each irradiation. For example, in a method of treating cancer, the nanoparticles may be administered to a subject and then irradiated one, two, three, four, five, or six times, daily or weekly following a single dose. Additional doses of the nanoparticles to maintain a desired concentration at the target site may be administered to the subject as needed over the course of treatment.

In one aspect, the nanoparticles may be attached to a targeting moiety specific for a tumor cell, such as an antigen binding protein (e.g., anti-EpCAM) or folate. Antigen binding proteins include, but are not limited to, antibodies, antibody fragments, antibody derivatives, antibody analogs, and fusion proteins, that bind a specific tumor cell antigen.

In addition to being used alone as therapeutic agents, the nanoparticles and compositions of the present invention may be used in combination with other therapies. Examples of antitumor therapies that can be used in combination with the nanoparticles and compositions include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferon, interleukin, tumor necrosis factor (TNF), hyperthermia and cryotherapy), agents to attenuate any adverse effect (e.g., antiemetics), gene therapy, oncolytic viruses, and any other therapeutic agent. In one aspect, animal survival can be improved by combining the nanoparticles with a therapeutic agent that inhibits a tumor cell's ability to mitigate oxidative stress.

Examples of therapeutic agents that may be administered with a nanoparticle or composition of the present disclosure include, but are not limited to, antitumor agents, antineoplastic agents, prodrugs, lysosome destabilizing agents (e.g., chloroquine), analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, antibiotics, anticoagulants, antidepressants, antiepileptics, antibacterials, antifungals, antifibrotic agents, anti-infective agents, anti-parasitic agents, antihistamines, antimuscarinic agents, antimycobacterial agents, antineoplastic agents, antiprotozoal agents, antiviral agents, cardiac drugs, anxiolytic sedatives, beta-adrenoceptor blocking agents, corticosteroids, cough suppressants, dopaminergics, hemostatics, hematological agents, hypnotics, immunological agents, muscarinics, neurological drugs, bioactive peptides, steroid hormones, nucleic acids, vaccines, anti-protozoan drugs, barbiturates, photosensitizer substances parasympathomimetics, prostaglandins, radio-pharmaceuticals, sedatives, stimulants, sympathomimetics, vitamins, xanthines, growth factors, hormones, antiprion agents, and combinations thereof. For example, the therapeutic agent may be an antitumor agent selected from the group consisting of an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; a mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a Flt-3 inhibitor; an Hsp90 inhibitor; a kinesin spindle protein inhibitor; a MEK inhibitor; an antitumor antibiotic; a nitrosourea, a compound targeting/decreasing protein or lipid kinase activity, a compound targeting/decreasing protein or lipid phosphatase activity, any further anti-angiogenic compound, and combinations thereof. Specific examples of antitumor agents include, but are not limited to, azacitidine, axathioprine, bevacizumab, bleomycin, capecitabine, carboplatin, chlorabucil, cisplatin, cyclophosphamide, cytarabine, daunorubicin, docetaxel, doxifluridine, doxorubicin, epirubicin, etoposide, fenretinide, fluorouracil, gemcitabine, herceptin, idarubicin, mechlorethamine, melphalan, mercaptopurine, methotrexate, mitoxantrone, oxaliplatin, paclitaxel, tafluposide, teniposide, tioguanine, retinoic acid, valrubicin, vinblastine, vincristine, vindesine, vinorelbine, receptor tyrosine kinase inhibitors, and combinations thereof. Additional examples of antitumor and other therapeutic agents are known in the art.

In one aspect, the nanoparticles or compositions of the present disclosure exert their antitumor activity via the induction of apoptosis or necrosis. Apoptotic cells may be identified by histological markers such as nuclear and cytoplasmic condensation and cellular fragmentation. Necrotic cells may be identified by histological markers such as cellular and organelle swelling, chromatin flocculation, loss of nuclear basophilia, degraded cytoplasmic structure, impaired organelle function, increased membrane permeability, and cytolysis. One mechanism for inducing apoptosis and/or necrosis involves the activation of initiator caspases (e.g., caspase-2, caspase-8, caspase-9, caspase-10), executioner caspases (e.g., caspase-3, caspase-6) and also pro-inflammatory caspases (e.g., caspase-1 and caspase-13). The role of the pro-inflammatory caspases in cell death is likely related to their ability to induce host inflammatory responses in vivo. Caspase activity can therefore be analyzed as a measure of apoptosis and/or necrosis. Other methods for detecting cell death via apoptosis and/or necrosis known in the art are also suitable for measuring the antitumor activity of the nanoparticles or compositions of the present disclosure, including Tdt-mediated dUTP nick-end labeling (TUNEL) assays, in situ end labeling (ISEL) assays, DNA laddering assays, DNA fragmentation assays, fluorescence-activated cell sorting (FACS)/flow cytometry analysis, microscopy analysis, cell staining (e.g., using trypan blue, propidium iodide, 7-actinomycin D, Annexin V, Hoescht, fluorescein diacetate-green, DAPI, and/or other dyes known in the art) assays, and enzyme-linked immunosorbent assays (ELISA).

Tumor growth also can be analyzed to determine the antitumor activity of the nanoparticles of the present disclosure. Tumor mass, volume, and/or length can be assessed using methods known in the art such as callipers, ultrasound imaging, computed tomography (CT) imaging, magnetic resonance imaging (MRI), optical imaging (e.g., bioluminescence and/or fluorescence imaging), digital subtraction angiography (DSA), positron emission tomography (PET) imaging and/or other imaging analysis. Tumor cell proliferation can also be analyzed using cellular assays that measure, e.g., DNA synthesis, metabolic activity, antigens associated with cell proliferation, and/or ATP. In various embodiments, the method of the present disclosure reduces the size of a tumor at least about 5% (e.g., at least about 10%, at least about 15%, at least about 25%, at least about 30%, at least about 40%, at least about 50%, at least about 60%, at least about 70%, or at least about 80%).

In addition to their use as anticancer agents, ROS-generating nanoparticles are generally useful in cell biology to reconstitute redox signaling mechanisms at high temporal and spatial resolution. Presently, redox signals are studied in cells by adding bulk reagents to samples. By illuminating specific regions of nanoparticle-labeled cells, it is possible to reconstitute localized ROS signals within living cells (D'Autréaux and Toledano, *Nat. Rev. Mol. Cell Biol.* 8:813-24 (2007)).

The present disclosure will be more readily understood by reference to the following examples, which are provided by way of illustration and are not intended to be limiting.

EXAMPLES

The following examples describe the preparation of nanoparticles of the present disclosure and use as therapeutic agents. For the experiments described herein, cell culture media and phosphate buffered saline (PBS) were obtained from Invitrogen Corp. (Carlsbad, Calif.). Cover-glass bottom dishes were purchased from MatTek Corp. (Ashland, Mass.). Unless otherwise noted, chemicals were obtained from Sigma Chemical Co. (St. Louis, Mo.). Organic solvents were obtained from Fisher Scientific (Pittsburgh, Pa.). Distilled, de-ionized $H_2O$ was used in all experiments. In vitro data are presented as the mean±s.d., and in all cases n>3. Data were evaluated with Student's t-test.

Example 1

Nanoparticle Characterization $WO_3$/Pt nanoparticles were prepared using photodeposition (Abe et al., supra), and their physical features were characterized. Briefly, $WO_3$ nanoparticles were suspended in a 30% MeOH/70% $H_2O$ solution, wherein MeOH served as a sacrificial electron donor. The suspension was mixed with solid chloroplatinic acid to give 2.7% Pt and then alkalinized with NaOH to a pH of about 12. The sample was deaerated by bubbling $N_2$ gas through the suspension for 20 minutes The sample was then stirred during illumination with a 200 W Hg—Xe lamp for 2 hours, followed by dialysis against $H_2O$. Nanoparticles were prepared using $WO_3$ having an orthorhombic crystal structure.

Figure 2A:
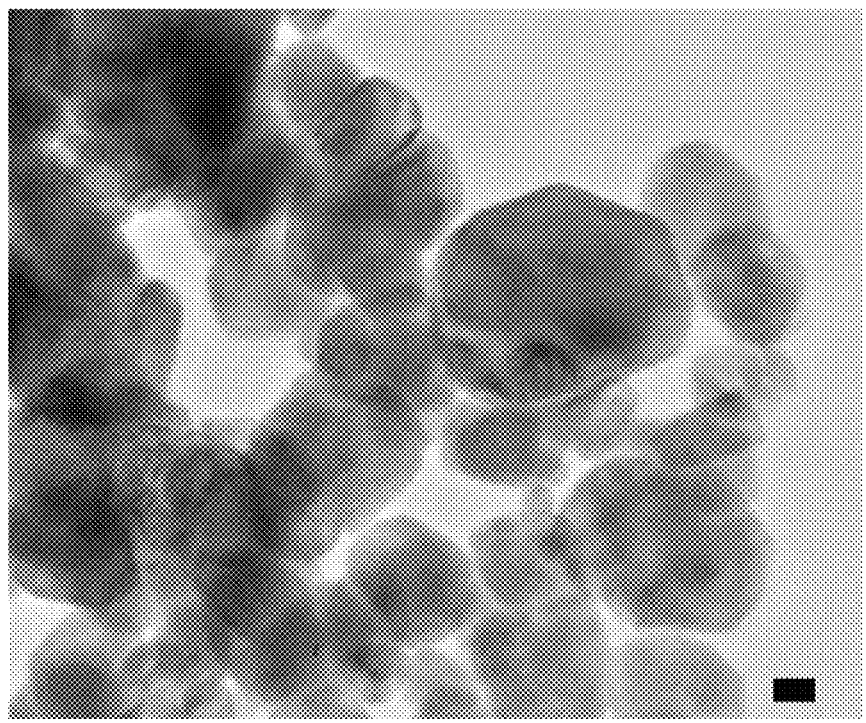
FIGS. 2A-2B depict electron microscopy of $WO_3$ nanoparticles with and without platinum cluster grafts.
Figure 2B:
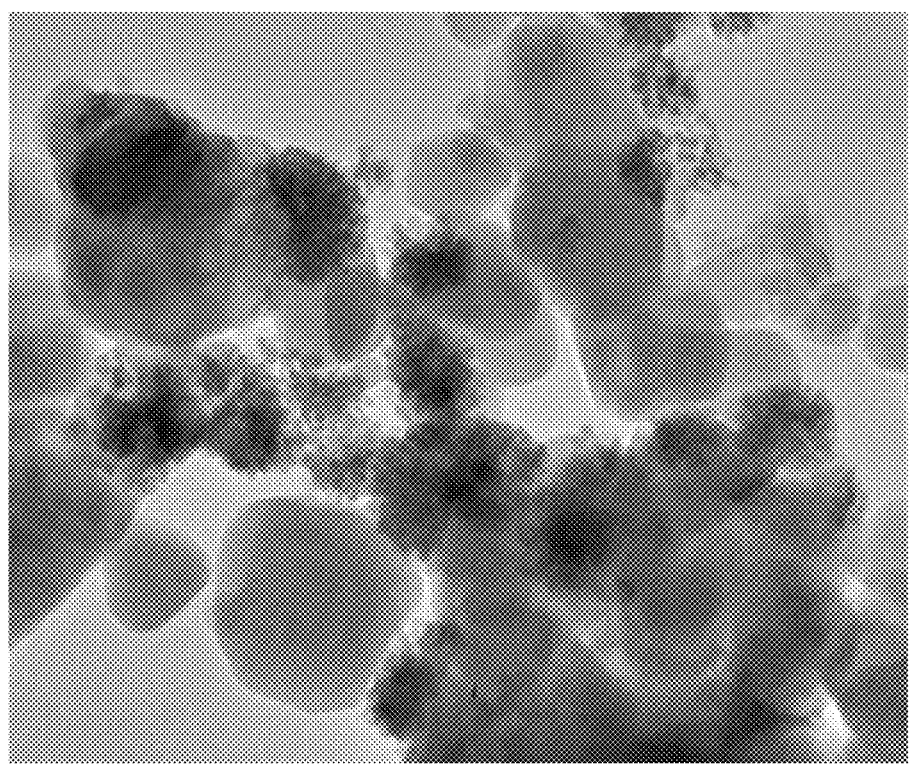

Nanoparticles were observed using a JEOL TEM-3011 transmission electron microscope (TEM) operated at 300 kV. Nanoparticles were dispersed in ethanol (~2 mg/ml) and a drop of suspension was deposited on a carbon-covered copper grid. FIG. 2A shows a high-resolution transmission electron microscopy (HR-TEM) of $WO_3$ nanoparticles, which had an average size of ~60 nm. FIG. 2B shows a HR-TEM micrograph of $WO_3$/Pt nanoparticles. Pt cluster grafts could be discerned by comparing FIGS. 2A and 2B. Each Pt cluster graft contained between 5 and 25 platinum nanospikes. The height to base ratio of the Pt cluster grafts was about 5:1. The nanoparticles' band-gap properties were confirmed using diffuse reflectance spectroscopy collected using a Shimadzu UV-2400 UV-visible spectrophotometer with a diffuse reflectance attachment (ISR-2000) (data not shown).

Figure 3:
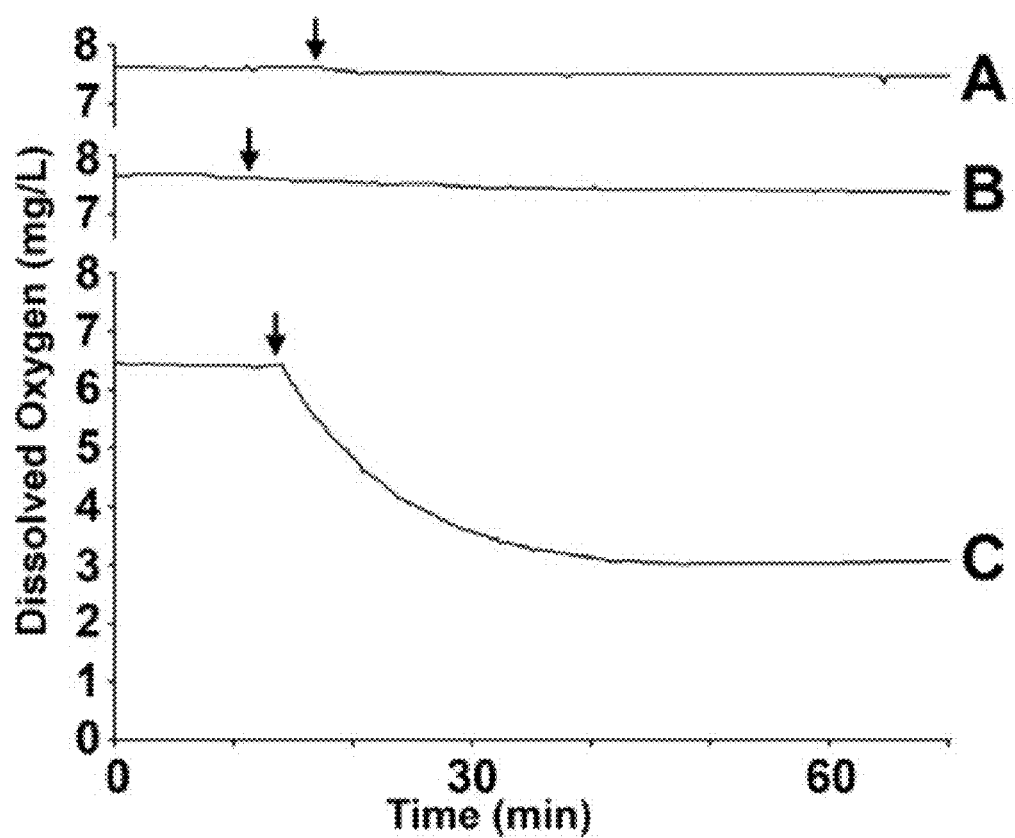
FIG. 3 depicts the utilization of the substrate oxygen by (A) a solution of 0.1% MeOH, (B) a suspension of $WO_3$/Pt nanoparticles in $H_2O$, and (C) a suspension of 0.5 mg/mL $WO_3$/Pt nanoparticles and 0.1% MeOH in water. Dissolved oxygen (mg/l) is plotted at the ordinate, whereas the abscissa lists time, and the initiation of exposure to light is indicated with an arrow.

The nanoparticles' functional properties were studied. To assess oxygen utilization during hydroxyl radical synthesis, the disappearance of dissolved $O_2$ was measured using a Clark electrode (Oakton model DO2700 meter, Cole-Parmer, Vernon Hills, Ill.). Samples were placed in customized Hach BOD bottles (Loveland, Colo.) for measurement. Instrument performance was verified using Zero Oxygen Standard tablets (Mettler-Toledo AG, Schwerzenbach, Switzerland). A Schott infrared filter was used. FIG. 3 illustrates the loss of dissolved $O_2$. Only minimal increases (e.g., 0.4° C.) in sample temperature were noted during continual monitoring of the reaction chamber throughout the experiments. $O_2$ was measured during illumination of $WO_3$/Pt nanoparticles (0.5 mg/ml) using 0.1% MeOH as a sacrificial electron donor. No change in dissolved oxygen was observed when a solution of 0.1% MeOH was exposed to light or when a suspension of nanoparticles in $H_2O$ was switched from darkness to light. In contrast, a rapid loss of dissolved oxygen was observed at the onset of illumination in samples containing both nanoparticles and methanol/water. As the availability of the substrate decreased with time, the reaction slowed over time.

Figure 4A:
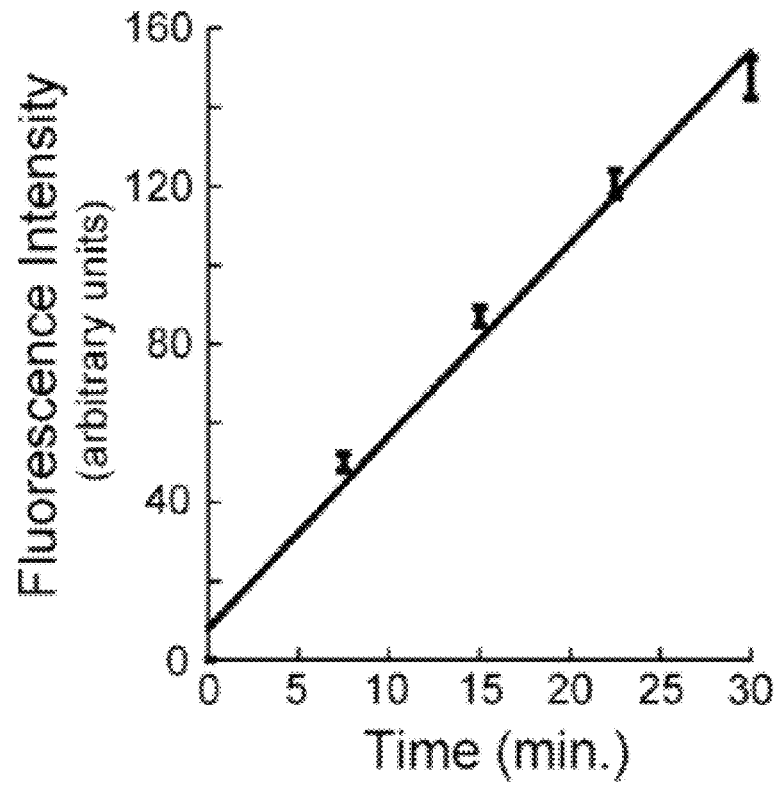
FIGS. 4A-4B depict the nanoparticles' ability to produce hydroxyl radicals. The fluorescence intensity of 7-Hydroxycoumarin, a fluorescent product of coumarin and hydroxyl radicals, is plotted at the ordinate, and the abscissa lists time.

Hydroxyl radical production by $WO_3$/Pt nanoparticles was also assessed using the coumarin assay (Ishibashi et al., *Electrochem. Commun.* 2:207-210 (2000)). Non-fluorescent coumarin molecules and hydroxyl radicals reacted to form the highly fluorescent 7-hydroxycoumarin, which was quantified using fluorescence measurements. Briefly, coumarin was dissolved at 1 mM in $H_2O$ by overnight stirring. $WO_3$/Pt nanoparticles were added to the solution and then illuminated with visible light from a 200 W Newport lamp with constant stirring. Aliquots were collected and assessed using fluorescence spectrophotometry with an emission wavelength of 460 nm and an excitation wavelength of 332 nm. FIG. 4A shows the kinetics of 7-hydroxycoumarin formation. The experiments demonstrated an increase in 7-hydroxycoumarin fluorescence over time and confirmed the nanoparticles' catalytic activity.

Figure 4B:
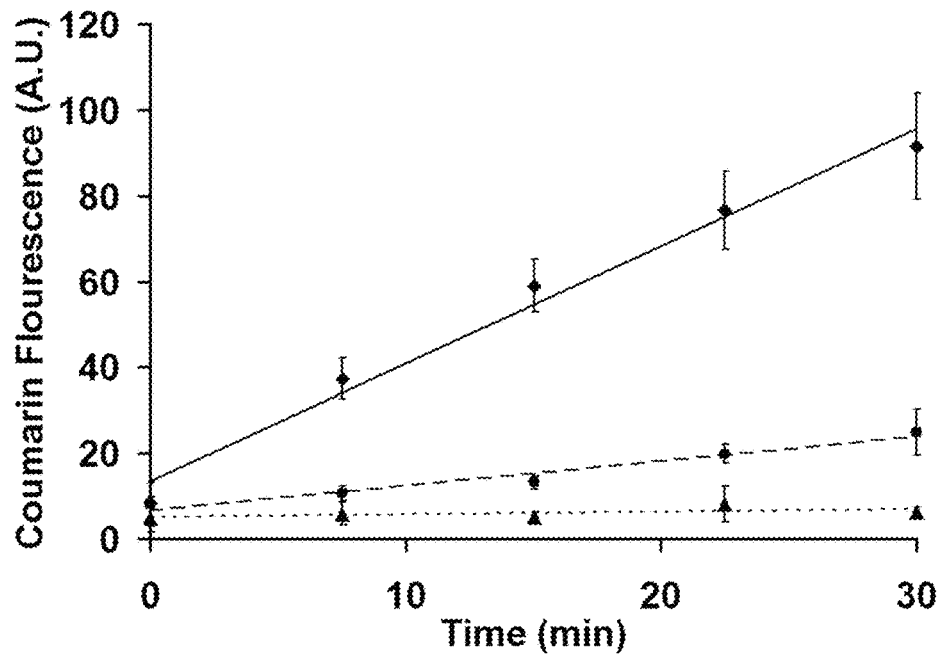

As a comparative example, $WO_3$/Pt nanoparticles were prepared using photodeposition as described above, but without adjusting the pH of the suspension to a pH of about 12. Instead, $WO_3$ nanoparticles were suspended in a 30% MeOH/70% $H_2O$ solution, and the suspension was mixed with solid chloroplatinic acid to give 2.7% Pt and a pH of about 2. FIG. 4B compares the kinetics of 7-hydroxycoumarin formation for $WO_3$/Pt nanoparticles prepared at alkaline pH and $WO_3$/Pt nanoparticles prepared at acidic pH. Hydroxyl formation experiments were carried out in an open reaction vessel containing 1 mM coumarin and 0.5 mg/ml $WO_3$/Pt nanoparticles. Aliquots were collected at various time points, centrifuged to remove catalyst, and then analyzed using a fluorescence spectrophotometer. The kinetics of 7-hydroxycoumarin fluorescence appearance was substantially greater using the nanoparticles prepared at alkaline pH of the disclosure in comparison to those produced at pH 2 under otherwise identical conditions. Unmodified $WO_3$ nanoparticles had insignificant levels of hydroxyl radical production.

In another comparative example, $WO_3$/Pt nanoparticles were prepared using $WO_3$ having a tetragonal crystal structure instead of an orthorhombic crystal structure. The relative fluorescence intensities of 7-hydroxycoumarin after 90 minutes of illumination were 222±27 fluorescence units for orthorhombic $WO_3$/Pt nanoparticles and 140±33 fluorescence units for tetragonal $WO_3$/Pt nanoparticles, a statistically significant difference. Additionally, there was no significant difference in hydroxyl radical production for orthorhombic $WO_3$/Pt nanoparticles having a folate surface modification, compared to orthorhombic $WO_3$/Pt nanoparticles without folate.

The nanoparticles' ability to act on complex organic molecules was evaluated. Spectrophotometric methods were employed to characterize organic compound degradation by $WO_3$/Pt nanoparticles. The dyes methyl orange and methylene blue were used because their degradation is mediated by valence band holes and can be monitored by spectrophotometry. Methyl orange is resistant to degradation by ROS, so its destruction is primarily mediated by valence band holes. Methyl orange was dissolved in $H_2O$ at a concentration of 128 µM at about pH 3, followed by the addition of 1 mg/ml $WO_3$/Pt nanoparticles. To insure oxygen availability, a pump was used to gently bubble air into the reaction chamber. A 200 W Newport lamp provided illumination. A water filter was interposed between the lamp and sample to prevent sample heating. Samples were stirred during illumination, and aliquots were periodically removed, centrifuged to remove catalyst, then read at 465 nm to monitor dye degradation. For the methylene blue assay, a suspension of 46.9 µM methylene blue and 0.5 mg/ml $WO_3$/Pt nanoparticles were stirred with aeration while illuminated. At various times, aliquots were collected and read at 660 nm. As noted by others (Qourzal et al., *J. Photochem. Photobiol. A: Chem.* 163:317-321 (2004)), direct photolysis of compounds in the absence of catalyst was small. Light absorption by the methyl orange was determined to be a linear function of concentration in the ranges used. Degradation data indicated the nanoparticle-mediated degradation of methyl orange was complete within 60 minutes. Degradation data were evaluated using the Langmuir-Hinshelwood equation: $\ln(C_0/C) = k_{app} \cdot t$, where $C_0$=initial concentration, C=concentration at time t, t=time, and, at low concentrations of dye, $k_{app}$=the product of the rate constant ($k_r$) and the apparent equilibrium constant for dye-nanoparticle binding ($K_e$). Quantitative analyses using Langmuir-Hinshelwood plots were linear, suggesting a first order reaction. Similar results were found in experiments utilizing methylene blue as substrate.

Figure 5:
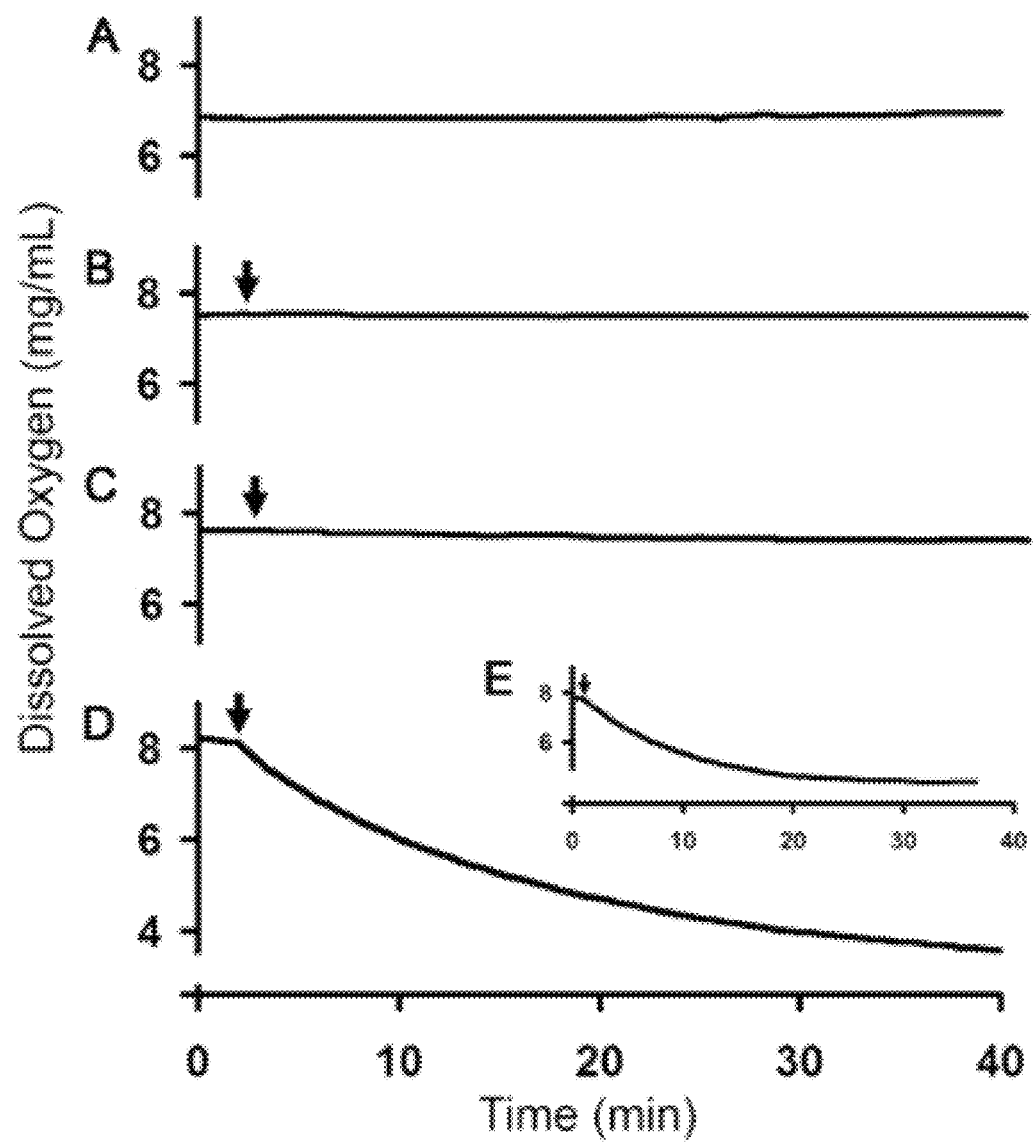
FIG. 5 depicts the utilization of the substrate oxygen by (A) a suspension of 0.5 mg/ml nanoparticles and 0.1% glucose in water exposed to darkness only, (B) a 0.1% glucose solution without nanoparticles, (C) illuminated nanoparticles in the absence of glucose, (D) a suspension of nanoparticles and glucose, and (E) a suspension of nanoparticles, glucose, and 100 mM t-butanol. Dissolved oxygen (mg/l) is plotted at the ordinate, whereas the abscissa lists time, and the initiation of exposure to light is indicated with an arrow.

To determine if biomolecules were acted upon by $WO_3$/Pt nanoparticles, glucose was incubated with nanoparticles in the presence of darkness or light. To distinguish between mechanisms of oxidative damage, t-butanol was included in reaction mixtures at 100 mM. T-butanol is an excellent scavenger of hydroxyl radicals, but a poor scavenger of valence band holes (Kim et al., *Environ. Sci. Techol.* 44:68496954 (2010)) and thus provided insight into the contributions of hydroxyl radicals and valence band holes in degradation reactions. The sample temperature was continually monitored during the experiment and found not to significantly change. As illustrated in FIG. 5, glucose contributed to $O_2$ utilization. The combination of nanoparticle, substrate, and light led to the disappearance of dissolved oxygen. Addition of the hydroxyl radical scavenger t-butanol, which was not a substrate for valence band holes, had minimal effect on the disappearance of oxygen. The data suggested that a significant fraction of the glucose molecules reacted with valence band holes, supporting that glucose was a substrate for valence band holes.

Example 2

Nanoparticle Uptake into Tumor Cells

Figure 6A:
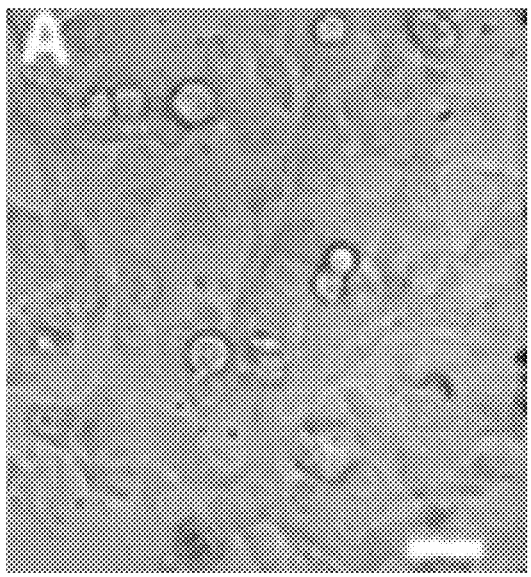
FIGS. 6A-6H depict micrographs of $WO_3$/Pt nanoparticles in association with tumor cells.
Figure 6B:
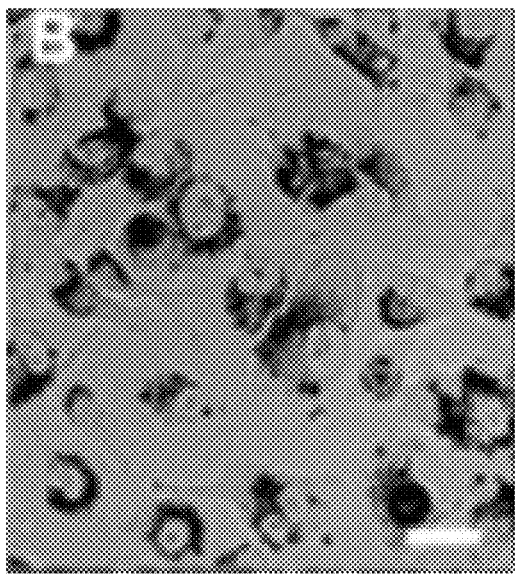

The murine 4T1 breast cancer cell line (Tao et al., *BMC Cancer.* 8:228 (2008)) was obtained from the American Type Culture Collection (Manassas, Va.). The cells were maintained on plastic tissue culture flasks in RPMI-1640 media (Invitrogen) containing 10% heat-inactivated FBS and 1% antibiotic/antimycotic. Cells were incubated 24 to 48 hours with $WO_3$/Pt nanoparticles (400 µg/ml). After removing free nanoparticles, samples were imaged with optical microscopy. Fluorescence microscopy was performed using a 20× (NA=0.5) or 40× (NA=0.6) Plan Fluor objective (Nikon, Melville, N.Y.) and an Andor iXon camera (Andor Technology, Belfast, Northern Ireland) attached to the bottom port of a Nikon TE2000-U inverted microscope with a 100 W mercury lamp. Images were captured and processed with Metamorph software (Molecular Devices, Downingtown, Pa.). Control experiments were conducted using cells grown in parallel, but without nanoparticles. Nanoparticles accumulated within tumor cells, as evidenced by the dark perinuclear accumulation of nanoparticles (FIG. 6B), but not in untreated cells (FIG. 6A).

Figure 6C:
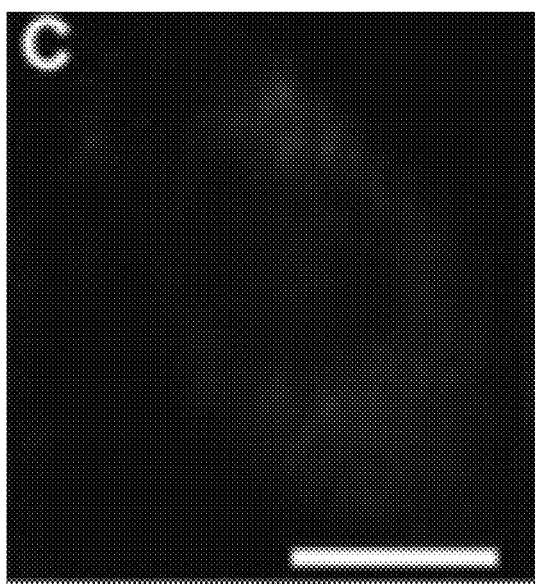
Figure 6D:
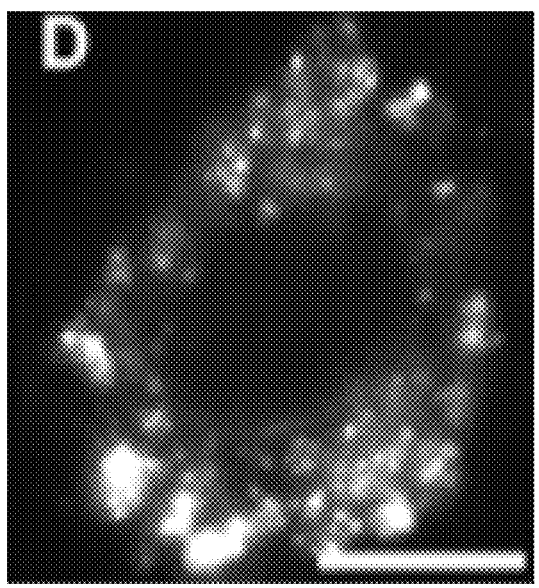
Figure 6E:

Similar studies were performed with surface plasmon resonance enhanced microscopy. To perform surface plasmon resonance enhanced microscopy (Vainrub et al., *Optics Lett.* 31:2855-7 (2006)), a CytoViva, Inc. (Auburn, Ala.) darkfield condenser (NA=1.2-1.4) and illumination source were attached to a Zeiss carrier for transmitted light illumination. A Zeiss Axiovert microscope equipped with a 100× darkfield objective (NA=1.6-1.3 NA) (Olympus) was employed. Surface plasmon resonance enhanced microscopy produced high contrast images that were captured as described above. Cells incubated in buffer did not demonstrate a significant signal using surface plasmon resonance enhanced microscopy (FIG. 6C). However, cells exposed to $WO_3$/Pt nanoparticles demonstrated intense scattering (FIG. 6D), thus indicating that the nanoparticles accumulated within the cytoplasm.

Figure 6F:
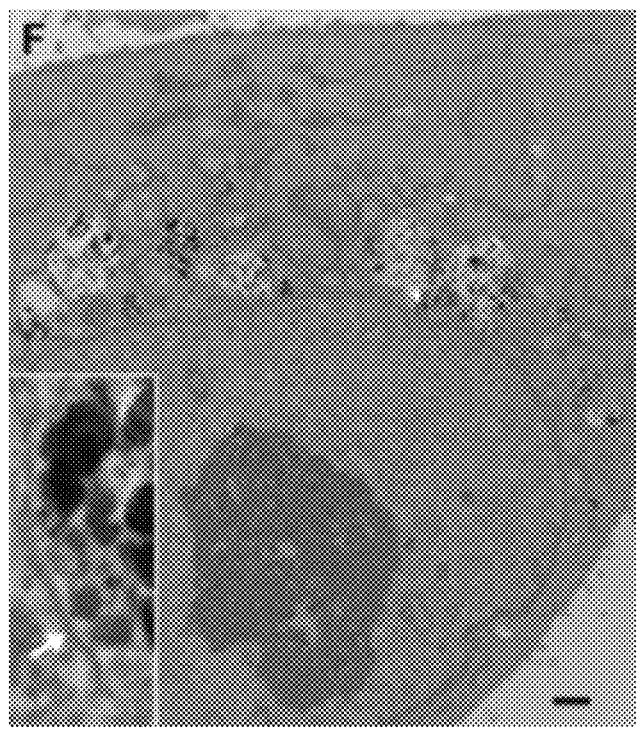
Figure 6G:
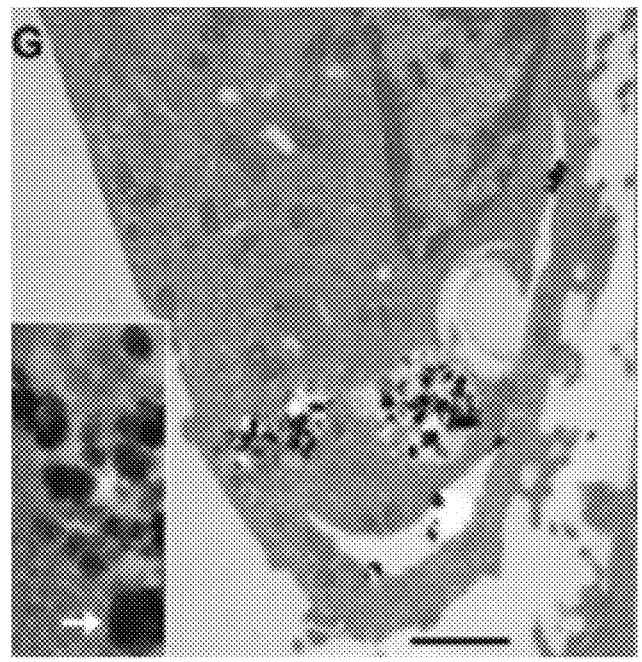
Figure 6H:
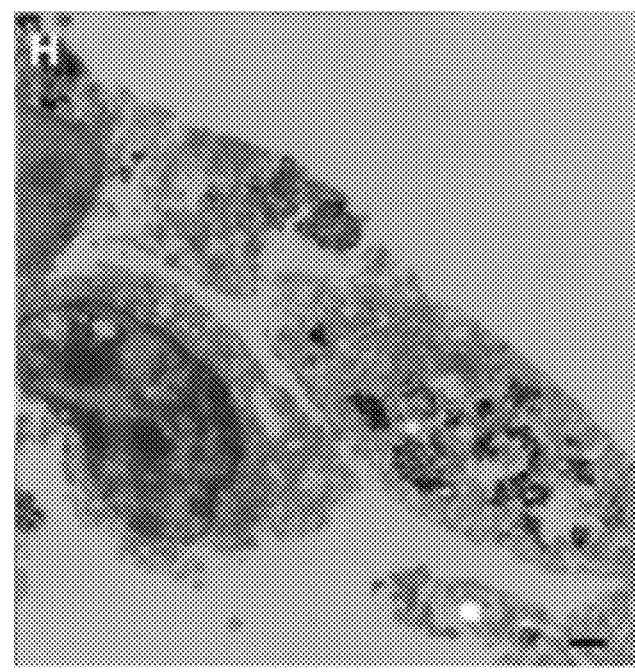

To identify the location of $WO_3$/Pt nanoparticles within cells, TEM studies of control and nanoparticle-treated cells were performed. Cell samples were fixed with 2% glutaraldehyde, washed thoroughly and then post-fixed with 2% osmium tetroxide (Polysciences, Warrington, Pa.). Samples were dehydrated in a graded ethanol series and then embedded in Spurr's resin. Thin sections were cut and then counterstained with lead citrate and uranyl acetate. Transmission electron micrographs were collected with a Philips CM-100 TEM. Due to their electron density, nanoparticles appeared as small black dots in the micrographs. FIG. 6F shows that nanoparticles accumulated in vacuolar compartments of tumor cells. As membranes could be seen at the periphery of the structures (FIG. 6F, insert and arrow), they appeared to be peri-nuclear endosomes. FIG. 6G shows a nanoparticle-treated tumor cell exposed to light therapy for 2 hours. Changes in cell morphology were apparent, including oddly-shaped vacuole-like structures. The insert in FIG. 6G shows a high magnification view at the periphery of a vacuole, and there was no indication that the vacuole was surrounded by a membrane structure; some nanoparticles appeared to extend into the cytoplasm (arrow). FIG. 6H shows a nanoparticle-treated tumor cell exposed to light therapy for 5 hours, which resulted in a loss of cell integrity.

To determine if the endosomes had matured to secondary lysosomes, tumor cells were incubated overnight with $WO_3$/Pt nanoparticles and labeled with the fluorogenic substrate Magic Red MR-(RR)2, which detected cathepsin B activity, as described by the manufacturer (Immunochemistry Tech., Bloomington, Minn.). Briefly, tumor cells on slides were exposed to substrate for 40 minutes, rinsed with buffer, and then observed by microscopy. Optical microscopy was performed on tumor cells tagged with $WO_3$/Pt nanoparticles and exposed to darkness or light. Imaging was performed using transmitted light or epi-fluorescence emission. Lysosomes appeared as punctate fluorescence whereas cytoplasmic staining was diffuse (Mediavilla-Varela et al., *Mol Cancer.* 8:68 (2009)). When maintained in darkness, the location of nanoparticles within cells was co-incident with cathepsin B labeling, which indicated the formation of secondary lysosomes and that many nanoparticles were delivered to secondary lysosomes. To assess the effect of nanoparticle activation on lysosome stability, cells were also exposed to light for 2 hr. prior to cathepsin B labeling. After a 2 hr. exposure to light, punctate cathepsin B staining was reduced dramatically, while diffuse labeling was increased in the cytosol, thus indicating lysosomal permeability.

Example 3

Response of Nanoparticle-Tagged Tumor Cells to Light In Vitro

Figure 7A:
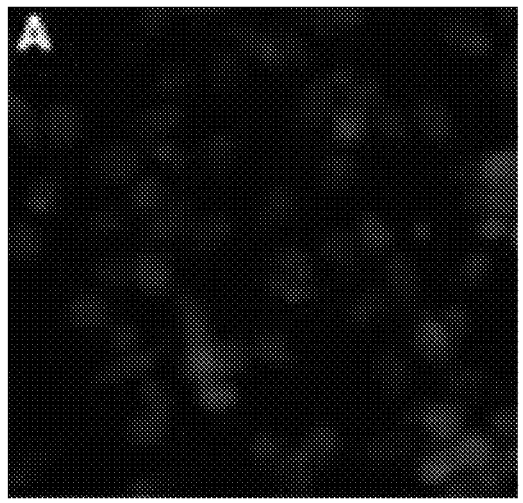
FIGS. 7A-7J depict characterization of biological responses to nanoparticles.
Figure 7B:
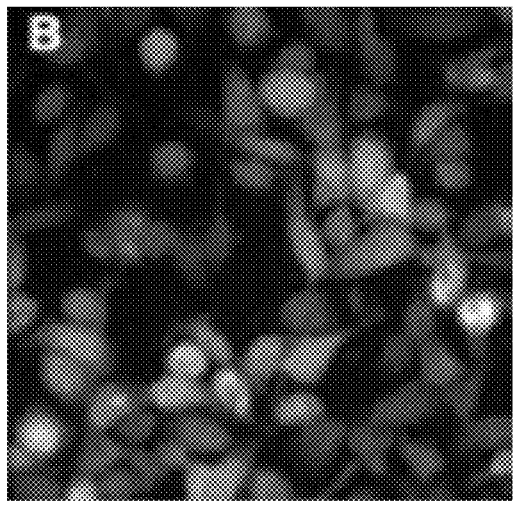

To confirm that $WO_3$/Pt nanoparticles retained catalytic activity within living cells, hydroxyl radical production was monitored using dihydrorhodamine 6G. Tumor cells were incubated with nanoparticles in the dark, as described above, and labeled with dihydrorhodamine 6G (Anaspec, Fremont, Calif.) (Qin et al., *Cell Biol Int.* 32:224-8 (2008)) in modified HBSS (10 mM HEPES, 1 mM $MgCl_2$, 2 mM $CaCl_2$, 2.7 mM glucose). Briefly, cells were incubated with 5 µg/ml dihydrorhodamine 6G for 10 minutes in the dark. Cells were thoroughly washed and illuminated for 30 minutes. Samples were observed using fluorescence microscopy to detect rhodamine 6G, the oxidized product of dihydrorhodamine 6G, that was formed by exposure to ROS (Qin et al., supra). To minimize the probe's photobleaching, a probe excited in the red was used and the incubation time was limited to 30 minutes (~0.6 lm/cm$^2$). In darkness, rhodamine 6G fluorescence was minimal (FIG. 7A). However, as shown in FIG. 7B, sample illumination led to substantial fluorescence, which demonstrated hydroxyl radical formation within cells.

Figure 7C:
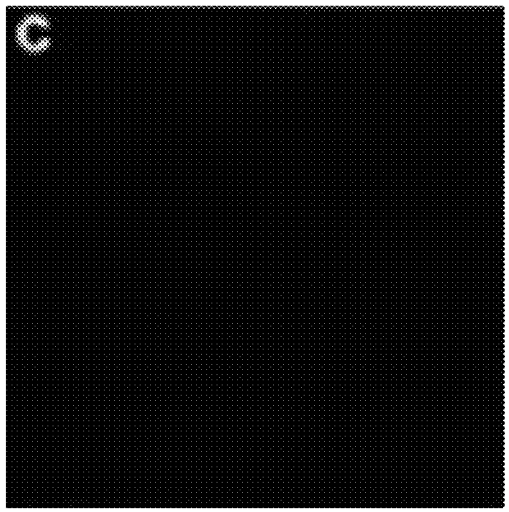
Figure 7D:
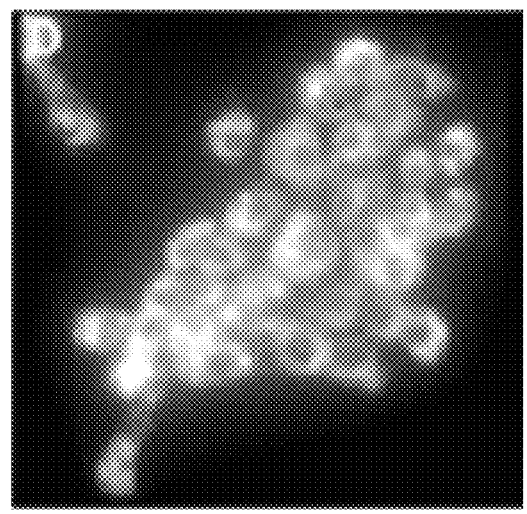

Since nanoparticles produced hydroxyl radicals within secondary lysosomes, the lysosomal membrane, which is rich in polyunsaturated fatty acids, was a likely target of these radicals. For confirmation, nanoparticle-tagged tumor cells were labeled with Liperfluo, a reagent that specifically detected lipid peroxides. Briefly, a solution of Liperfluo (N-(4-diphenylphosphinophenyl)-N'-(3,6,9,12-tetraoxatridecyl)perylene-3,4,9,10-tetracarboxydiimide) (Dojindo, Inc., Rockville, Md.) was made using DMSO as solvent (Yamanaka et al., *RCS Adv.* 2:7894-7900 (2012)). Tumor cells were washed with modified HBSS, and Liperfluo was added at 20 µM for 30 minutes at 37° C. Cells were then kept in the dark or illuminated for 20 minutes. Cells were observed using a fluorescein filter set and observed after 20 minutes in darkness or visible light. Although lipid peroxidation was not observed in darkness (FIG. 7C), extensive conversion of Liperfluo was observed after illumination (FIG. 7D), especially in the peri-nuclear region.

Figure 7E:
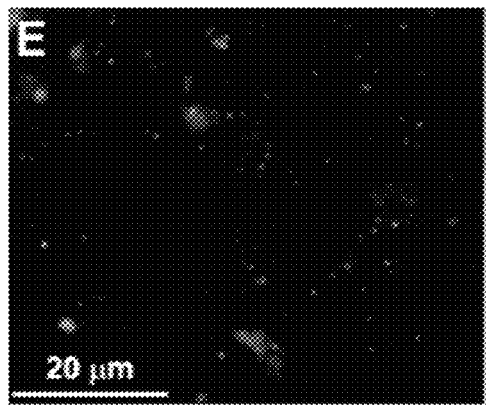
Figure 7F:
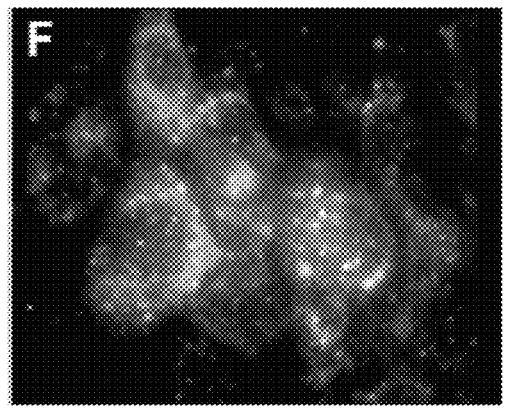
Figure 7G:
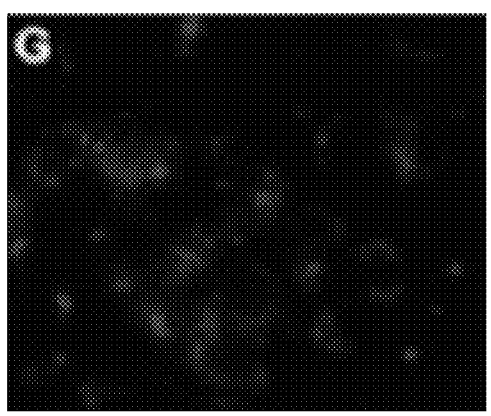
Figure 7H:
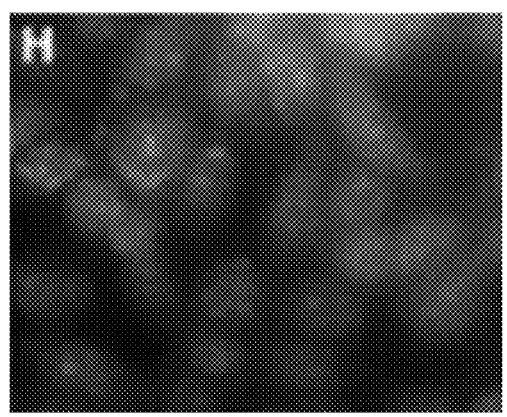

A key toxic product of lipid peroxidation is 4-hydroxynonenal (4-HNE), which reacts with biomolecules to block cell functions. To assess 4-HNE-mediated protein damage, cells were incubated with or without light exposure for 2 hours and labeled with anti-4-HNE-cysteine adduct antibodies. As FIG. 7E shows, 4-HNE-adducts were not observed in samples incubated in darkness, but were observed in cells exposed to light (FIG. 7F). Because lipid peroxide production damages lipid bilayers, lysosome stability was tested using a Lyso-ID Red protocol (Enzo Life Sci., Farmingdale, N.Y.). Briefly, after exposure to illumination or darkness, samples were incubated with a 1:1000 dilution of the stock solution provided by the manufacturer for 20 minutes at 37° C., followed by fluorescence microscopy. When incubated in the dark, the low pH of lysosomes promoted accumulation of the Lyso-ID Red, leading to lysosomal fluorescence with minimal cytoplasmic fluorescence (FIG. 7G). However, after incubation in light, lysosomal staining was reduced, while cytoplasmic fluorescence was enhanced. The data indicated that lysosomal membranes were not intact after illumination. Hence, ROS-mediated lipid peroxidation and attendant lysosome instability appeared to contribute to cell death.

Figure 7I:
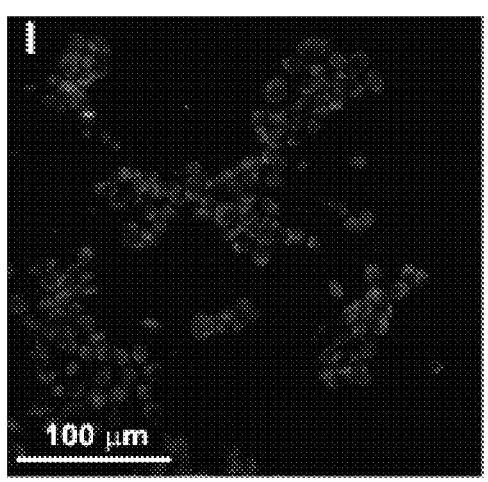
Figure 7J:
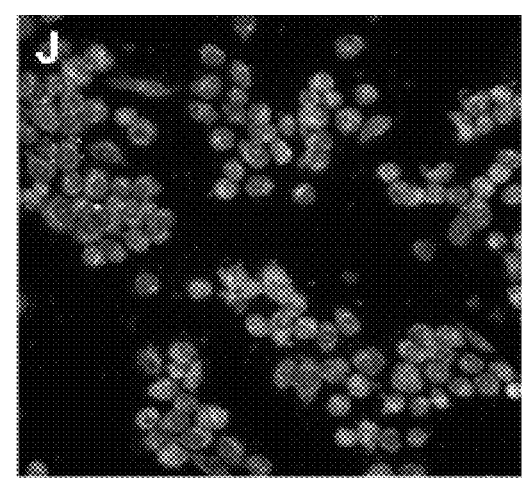
Figure 8A:
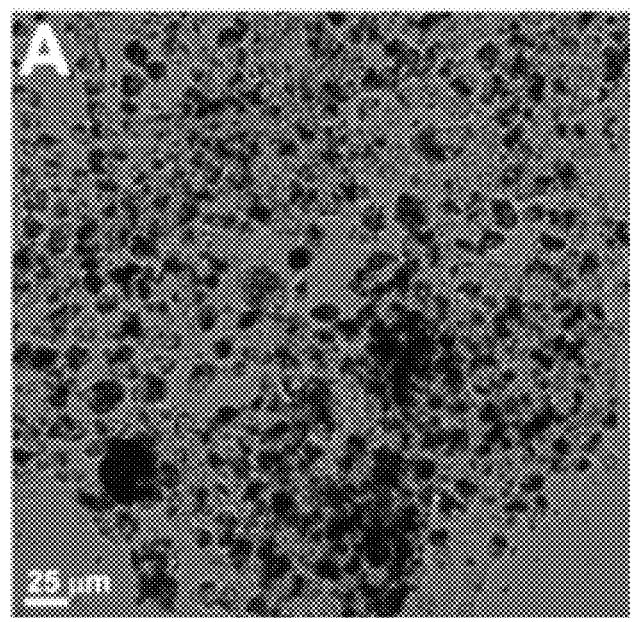
FIGS. 8A-8E depict detection of light-dependent aldehyde production within cells containing $WO_3$/Pt nanoparticles.
Figure 8B:
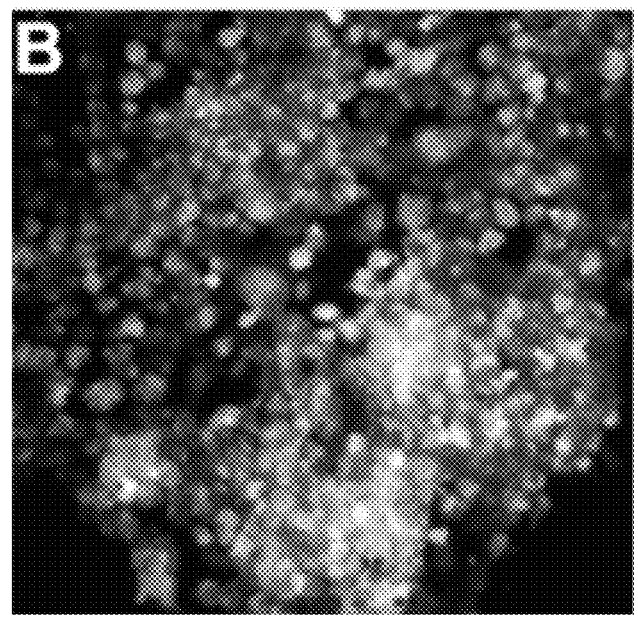
Figure 8C:
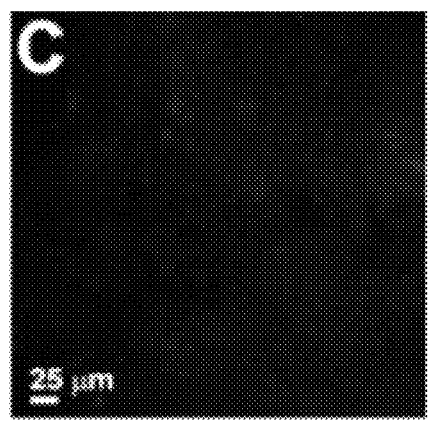
Figure 8D:
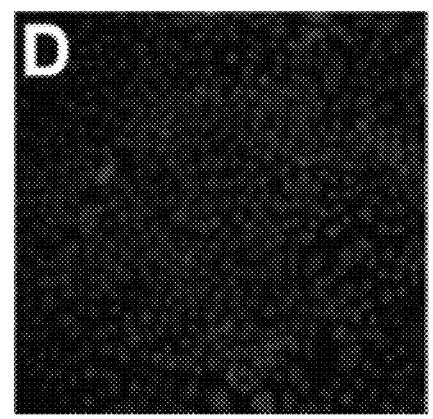
Figure 8E:
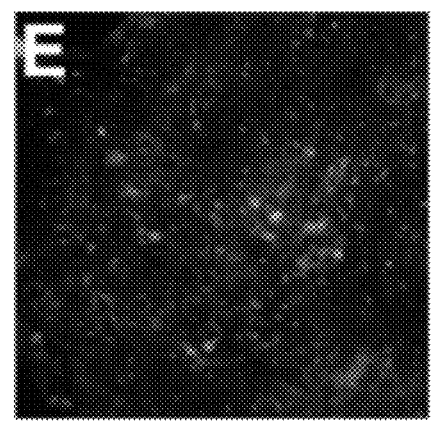

The effect of visible light on apoptosis of $WO_3$/Pt nanoparticle-treated cells was measured using a caspase activation assay. Samples were labeled using the FAM-FLICA caspase 3/7 inhibitor kit as described by the manufacturer (Immunochemistry Tech.). After washing to remove unbound inhibitor, samples were examined using fluorescence microscopy. FIGS. 7I and 7J show the light-dependent activation of caspase 3/7 in nanoparticle-treated tumor cells. After a 6 hr. exposure to darkness, caspase 3/7 activation was not observed (FIG. 7I). However, after visible illumination (51 J/cm$^2$) most cells displayed caspase 3/7 activation (FIG. 7J). A change in cells to the spherical shape associated with apoptosis was also noted in cells expressing activated caspase 3 (data not shown). Samples were fixed using 3.7% paraformaldehyde overnight, then washed with PBS. Samples were blocked with Image-iT FX (Invitrogen) for 30 minutes followed by the endogenous biotin blocking kit (Invitrogen) and labeled for 1 hr. with an activated caspase 3 antibody (Bioss, Woburn, Mass.). After rinsing with PBS, samples were incubated for 1 hr. with biotin-XX-conjugated goat anti-rabbit IgG (Invitrogen). Cells were washed followed by a 30-minute treatment with Alexa Fluor 594-conjugated streptavidin (Invitrogen). After streptavidin treatment, cells were washed and imaged. Apoptosis was also verified using an antibody directed against an activation epitope of caspase 3. For visualization of Michael adducts, samples were fixed for 15 minutes with DSP, extracted for 2 minutes with 100% ethanol, then fixed with 3.7% paraformaldehyde for 20 minutes. Samples were then blocked with 3% BSA for 1 hr. followed by 30 minutes with Image-IT FX (Invitrogen). Samples were labeled using a 4-HNE Michael adducts antibody (EMD Millipore, San Diego, Calif.). Second step labeling was performed as described above. A dramatic increase in caspase 3 activation was observed.

The 3-hydroxyl-2-naphthoic acid hydrazide (NAH) cytochemical method was used to test aldehyde reactivity in cell samples. Aldehydes, a lipid peroxidation product, were detected using the 2-OH-3-naphthoic acid hydrazide (NAH) reaction (Pompella and Comporti, *Am J Pathol.* 142:1353-7 (1993)). Briefly, cells were fixed with 5% trichloroacetic acid for 1 minute then washed 4 times with saline for 5 minutes each. Fixed samples were exposed to the staining solution (0.1% NAH solution in 50% ethanol containing 5% acetic acid) for 1 hr. at 60° C. Samples were then washed with 50% ethanol. The fluorescent reaction product was visualized using an optical filter set comprised of a 450DF65 nm excitation filter, a FITC dichroic reflector, and a long-pass 510ALP emission filter. FIG. 8 shows nanoparticle-tagged and untagged tumor cells incubated in darkness or light for 3 hr. followed by NAH staining. Dark clusters indicated regions of accumulated nanoparticles. All regions of the cells exhibited aldehyde reactive sites, an indicator of oxidative damage. The regions containing nanoparticles exhibited the greatest fluorescence intensity. In the presence of nanoparticles, light exposure dramatically increased NAH staining (FIG. 8B), thus indicating the formation of aldehyde reactive groups.

Similar findings were obtained using the aldehyde-reactive probe O-(biotinylcarbazoylmethyl)hydroxylamine followed by FITC-avidin labeling. Aldehyde sites were detected within cells using the Aldehyde Site Detection Kit (Cayman Chemical, Ann Arbor, Mich.). Cells (4T1) were incubated with or without nanoparticles, followed by exposure to darkness or light. Cells were then exposed to fixation, reacted with ARP, and labeled with FITC-avidin, as described by the manufacturer. O-(biotinylcarbazoylmethyl)hydroxylamine was used to tag aldehydes and FITC-avidin was used to visualize the sites. All regions of the nanoparticle-treated cells exposed to light exhibited aldehyde reactive sites, an indicator of oxidative damage. As expected, regions containing nanoparticles exhibited the greatest fluorescence intensity. Nanoparticle-treated cells exposed to darkness only or cells that were not incubated with nanoparticles did not exhibit fluorescence. The data indicated a pathway in which hydroxyl radical production activated lipid peroxidation pathways and oxidative cell damage in cells treated with nanoparticles activated with light.

Example 4

In Vivo Activity of Nanoparticles

The ability of $WO_3$/Pt nanoparticles to influence tumor cells in a model of breast cancer metastasis to the eye's anterior chamber was tested (McKenna and Kapp, *J. Immunol.* 177:1599-608 (2006) and Niederkorn, J. Y., *Invest. Ophthalmol. Vis. Sci.* 25:1080-6 (1984)). On the day preceding ocular injections, $2.5 \times 10^6$ 4T1 cells were mixed with 1 mg of $WO_3$/Pt nanoparticles and then plated overnight in a 60 mm dish. On the following day, the nanoparticle-labeled cells were removed from the plate and washed with media and PBS to remove unbound nanoparticles. Cells were re-suspended in 250 µl of PBS to a final concentration of $10^4$ cells per µl. After administration of anesthesia, an incision was made in the left cornea near the dorsal edge and then, using a 29 gauge needle, some inter-ocular fluid was allowed to escape. Using a 2 µl Hamilton syringe with a blunt needle, 1 µl of cells ($10^4$ cells) were injected through the incision. Both eyes were covered with ophthalmic ointment to prevent drying. Each mouse was placed in a separate cage until fully ambulatory and then returned to a standard housing cage.

Figures 9A, 9B, 9C, 9D, 9E:
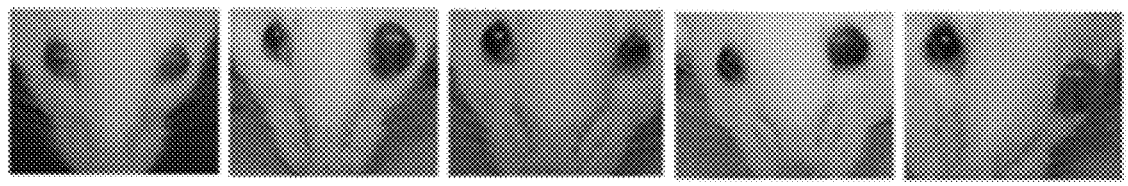
FIGS. 9A-9E depict external photographs of murine eyes following treatment with tumor cells with or without nanoparticles injected into the animal's left eye.
Figure 10A:
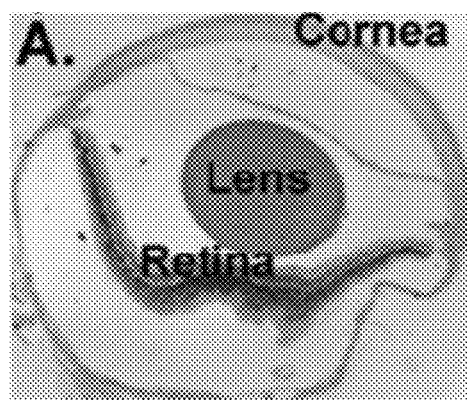
FIGS. 10A-10C depict sections of eyes following treatment with tumor cells with or without nanoparticles. "T" represents areas of tumor growth.
Figure 10B:
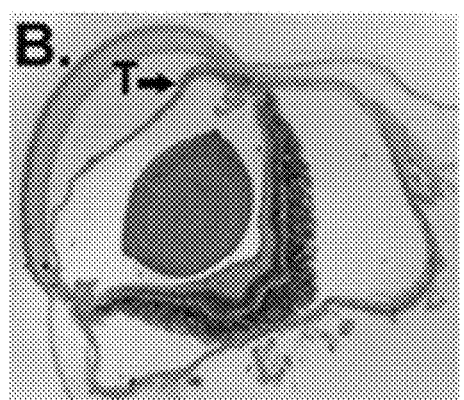

Untreated eyes and eyes treated with nanoparticles alone did not show tumors. Significant tumor growth was evident for 4T1-treated animals, which survived 14 to 16 days (FIG. 9). In some experiments, mice treated with 4T1 cells and $WO_3$/Pt nanoparticles were kept in constant darkness, and the mice exhibited large tumors that were indistinguishable from the positive controls. Mice treated with $WO_3$ nanoparticles which lacked Pt also exhibited large tumors by day 16 (FIG. 9C). Subsequent histochemistry confirmed the presence of tumor cells in animals. Tissue was fixed in 4% buffered paraformaldehyde, embedded in paraffin and cut into 5 µm thick sections. Sections were stained with hemaoxylin/eosin and visualized with transmitted light microscopy. In contrast, nanoparticle-treated animals exposed to ambient light demonstrated small tumor burdens at 2 weeks (FIG. 10B).

Figure 10C:
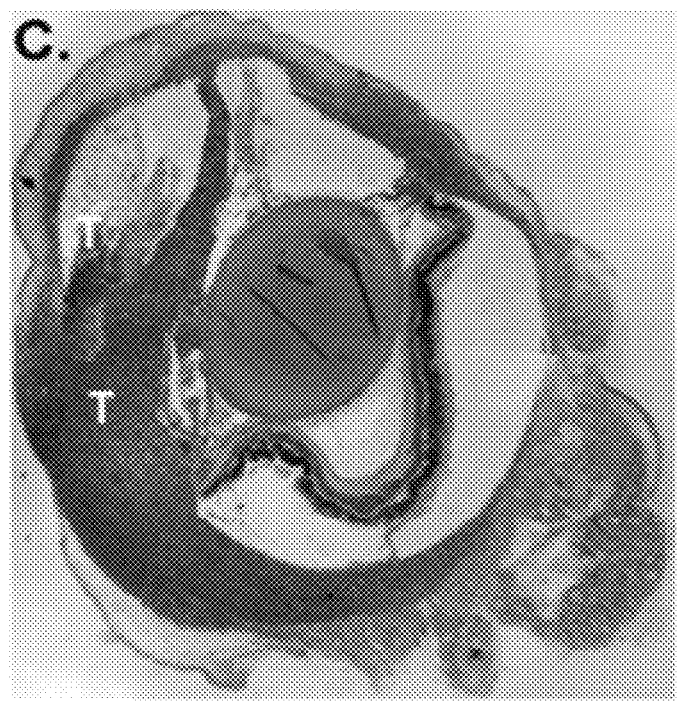
Figure 11:
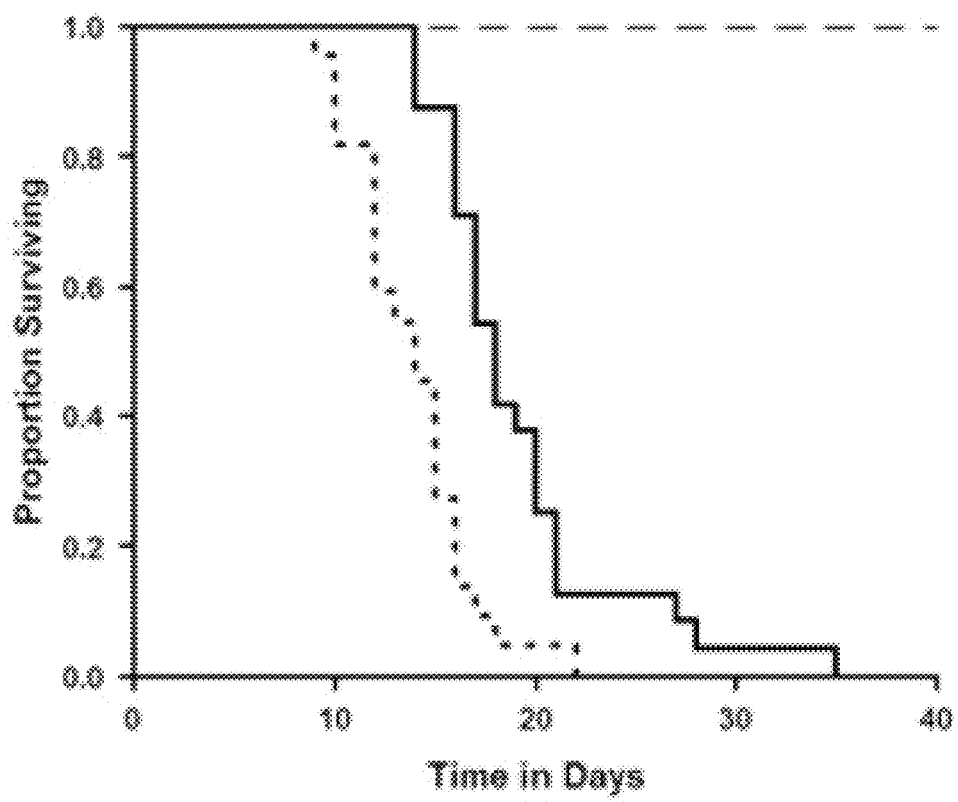
FIG. 11 depicts the survival curve of 4T1 cell-treated mice (n=22) (dotted line), mice exposed to 4T1 cells and nanoparticles and light therapy (n=24) (solid line), and mice treated with nanoparticles only, without administration of tumor cells (n=16) (horizontal dashed line). The survival curves differ significantly, as judged by Kaplan-Meier statistical tests (P<0.0001), for the comparison of each pair.
Figure 12:
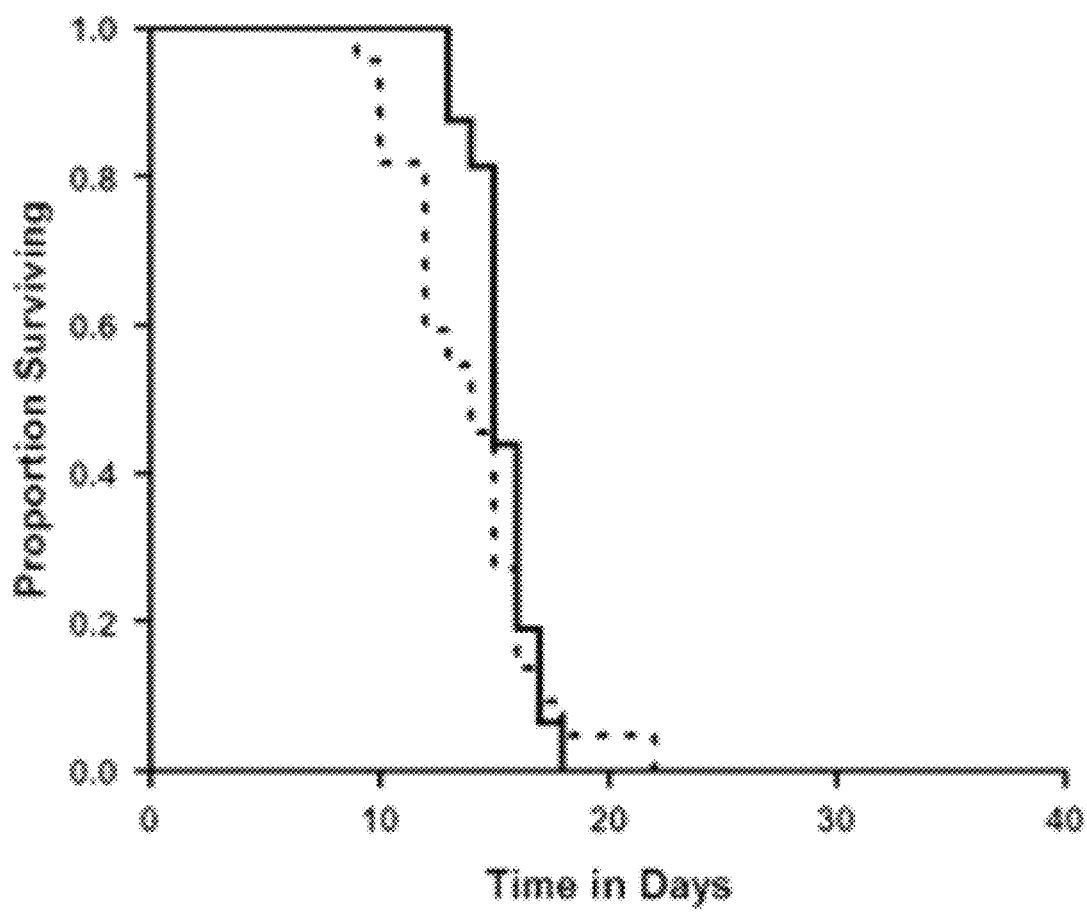
FIG. 12 depicts survival curves of mice following treatment with WO$_3$/Pt nanoparticles. The survival of mice treated with tumor cells alone (n=22) (dotted line) was not significantly different from that of nanoparticle-treated 4T1 cells in mice kept in the dark (n=16) (solid line).

Animal survival following treatment with PDT was evaluated. Light therapy was performed using a LED lamp assembly. Briefly, three royal blue (447 nm) Luxeon Star Rebel LEDs (6370 mW @ 700 mA) (Quadica Developments, Inc., Brantford, Ontario) were mounted in a ventilated plexiglass box using heat sinks and optical diffusers on each LED. The LEDs were mounted to provide an approximately uniform and overlapping illumination area. A fan was mounted on the apparatus to remove heat. An adjustable power supply/timer was constructed to drive the fan and LEDs. An illuminance of 0.6 $lm/cm^2$, which was small compared to daylight exposure, was employed to treat animals; exposure times were 30 minutes on the day of injection and 45 minutes twice weekly thereafter. Murine survival curves were evaluated using Kaplan-Meier analysis (KMWin) (Gross et al., *PLoS One.* 7:e38960 (2012)). All findings concerning experimental and control mice were included in the data presented. FIG. 10C shows a section of an eye treated with tumor cells alone. Tumor growth in the anterior chamber was indicated with a "T", and extensive infiltration of neighboring structures was observed. FIG. 11 shows survival curves of control and light-treated mice bearing nanoparticle-tagged tumor cells (90 minutes of PDT/wk.) (P<0.0001). There was no difference between mice exposed to nanoparticle-labeled tumor cells kept in the dark and untreated tumor-bearing mice (P=0.6) (FIG. 12). When the anterior chambers of Balb/c eyes were treated with 8 µg of nanoparticles, which equaled the amount used in the 4T1 experiments, no change in animal survival was noted (FIG. 11). Thus, the nanoparticles, under these conditions, were not inherently toxic to mice, yet could significantly reduce the tumor burden when activated.

The foregoing Examples demonstrated that $WO_3$/Pt nanoparticles according to the present disclosure combined with visible light potentiated tumor cell destruction. $WO_3$/Pt nanoparticles, which produced ROS and degraded organic compounds, mediated tumor cell death in vitro and reduce tumor growth in vivo. Nanoparticle delivery to the tumor cells' secondary lysosomes allowed for local hydroxyl radical production, lipid peroxidation, and activation of the lysosomal membrane permeabilization pathway of cell death (Boya and Kroemer, *Oncogene.* 27:6434-51 (2008)). On the basis of experiments measuring dissolved oxygen disappearance, the turnover number of a $WO_3$/Pt nanoparticle (2500 $sec^{-1}$) was about 20 times greater than that of the activated NADPH oxidase (120-150 $sec^{-1}$) of leukocytes (Cross et al., *Biochem. J.* 338 (Pt 1):229-33 (1999)). However, this overestimated NADPH oxidase activity because the leukocyte response was transient and it was blunted by the reduced extracellular pH within tumors (Gerweck and Seetharaman, *Cancer Res.* 56:1194-8 (1996) and Araki et al., *Cancer Res.* 51:3212-6 (1991)). The turnover numbers of $WO_3$/Pt nanoparticles for methylene blue and methyl orange were higher than some degradative protein enzymes (e.g., 1.4- to 3000-fold higher than β-galactosidase, chymotrypsin, pepsin, and ribonuclease). To illustrate the nanoparticle's biochemical impact, an illuminated 0.2 μm diameter endosome containing 50 nanoparticles would, in the absence of other reactions and transmembrane diffusion, accumulate hydroxyl radicals to a local concentration of 10 M in one hour. Thus, the functional activities of the nanoparticles compared favorably with biological enzymes.

The induction of cell death mechanisms by the nanoparticles of the present disclosure provide a novel means of managing different types of cancer, including ocular and skin cancer. Nanoparticles comprising a metal oxide and a platinum cluster having a height to base ratio greater than 1, in a light-dependent fashion, reduce the tumor growth in a model of late-stage breast cancer metastasis. Animal studies indicate that, in the presence of light, nanoparticles reduce the tumor burden. Survival is significantly enhanced using nanoparticle-tagged tumor cells in the presence of illumination compared to untreated animals or animals kept in the dark. The survival time extension of nanoparticle-treated mice is comparable to the life extension of 4T1-bearing Balb/c mice in a model testing simultaneous treatment with multiple chemotherapeutic agents (Bao et al., *Am. J. Pathol.* 178:838-52 (2011)). Because the nanoparticles can be activated with visible light to produce hydroxyl radicals within tumor cells, stimulate lipid peroxidation, promote lysosomal membrane permeabilization, and activate apoptosis, they provide an improved therapeutic option useful for treating cancer.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A nanoparticle comprising a metal oxide and a photocathode comprising one or more platinum clusters comprising about 1 to about 100 platinum nanospikes attached to the surface of the metal oxide, wherein each nanospike comprises more than 60 platinum atoms linked by metallic bonding, wherein the platinum cluster has a height to base ratio greater than 1, wherein the metal oxide is tungsten trioxide having an orthorhombic crystal structure.

2. The nanoparticle of claim 1, wherein the platinum cluster is a co-catalyst in the formation of reactive oxygen species and has a height to base ratio in a range of about 1 to about 2, about 2 to about 4, or about 2.5 to about 5.

3. The nanoparticle of claim 1, wherein the platinum cluster comprises platinum oxide.

4. The nanoparticle of claim 1, wherein the crystal structure of the platinum cluster is not cubic.

5. The nanoparticle of claim 1, wherein the surface-to-volume ratio of the platinum cluster is greater than 1 $nm^{-1}$.

6. The nanoparticle of claim 1, wherein the diameter of the nanoparticle is greater than about 20 nm, optionally about 50 nm to about 60 nm.

7. The nanoparticle of claim 1, wherein the platinum cluster comprises about 1 to about 100 nanospikes having a base width of about 1 nm to about 10 nm and/or a height of about 5 nm to about 20 nm.

8. The nanoparticle of claim 1, wherein the platinum cluster comprises a platinum oxide, optionally, PtO, $PtO_2$, $PtO_3$, or $Pt_3O_4$.

9. A composition comprising the nanoparticle of claim 1 and a pharmaceutically acceptable carrier.

10. A method of making nanoparticles comprising tungsten trioxide and a photocathode comprising one or more platinum clusters comprising about 1 to about 100 nanospikes attached to the surface of the tungsten trioxide, wherein each nanospike comprises more than 60 platinum atoms linked by metallic bonding, wherein the platinum cluster has a height to base ratio greater than 1, said method comprising mixing tungsten trioxide nanoparticles having an orthorhombic structure with chloroplatinic acid to form a mixture, and alkalinizing the mixture to a pH above 10.

11. The method of claim 10, comprising alkalinizing the mixture to a pH of about 12.

12. A nanoparticle formed using the method of claim 10.

13. A method of generating reactive oxygen species (ROS) in a cell, comprising irradiating an aqueous solution comprising the cell and the nanoparticle of claim 1 with radiation having a wavelength greater than about 400 nm.

14. A method of photodynamic therapy, comprising administering a therapeutically effective amount of the nanoparticle of claim 1 to a subject in need thereof and irradiating the nanoparticle with radiation having a wavelength greater than about 400 nm.

15. A method of treating cancer in a subject in need thereof comprising administering a therapeutically effective amount of the nanoparticle of claim 1 to the subject and irradiating the nanoparticle with radiation having a wavelength greater than about 400 nm.

16. The method of claim 15, wherein the cancer is selected from the group consisting of breast cancer, ocular cancer, skin cancer, bladder cancer, esophageal cancer, and lung cancer.

17. The method of claim 15, wherein the nanoparticle is administered intratumorally, intravenously, intraocularly, topically, or subcutaneously.

* * * * *